(12) United States Patent
Beaty et al.

(10) Patent No.: US 8,087,935 B2
(45) Date of Patent: Jan. 3, 2012

(54) IMPLANT DELIVERY SYSTEM

(75) Inventors: Keith D. Beaty, Jupiter, FL (US);
Richard J. Lazzara, Lake Worth, FL (US); Daniel J. Tarullo, Jupiter, FL (US); Thomas S. Heylmun, Meriden, CT (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 290 days.

(21) Appl. No.: 12/074,124

(22) Filed: Feb. 28, 2008

(65) Prior Publication Data
US 2008/0153062 A1 Jun. 26, 2008

Related U.S. Application Data

(60) Division of application No. 10/641,389, filed on Aug. 14, 2003, now Pat. No. 7,344,376, which is a division of application No. 09/812,161, filed on Mar. 19, 2001, now Pat. No. 6,619,958, which is a continuation-in-part of application No. 09/416,221, filed on Oct. 12, 1999, now Pat. No. 6,203,323, which is a continuation of application No. 09/057,087, filed on Apr. 8, 1998, now Pat. No. 5,964,591.

(60) Provisional application No. 60/043,131, filed on Apr. 9, 1997.

(51) Int. Cl.
*A61C 3/00* (2006.01)
*A61C 8/00* (2006.01)

(52) U.S. Cl. ........................................ 433/141; 433/173

(58) Field of Classification Search .................. 433/141, 433/173, 163, 174–176, 201.1, 202.2, 215, 433/220, 221; 81/451; 206/368–370, 63.5
See application file for complete search history.

(56) References Cited

U.S. PATENT DOCUMENTS

| 3,760,502 A | | 9/1973 | Hirsch | ................................ 32/8 |
| 3,897,703 A | * | 8/1975 | Phipps | ........................ 81/177.75 |
| 3,997,053 A | * | 12/1976 | Bondhus | ........................ 206/377 |

(Continued)

FOREIGN PATENT DOCUMENTS
EP     0 657 146 A1     6/1995
(Continued)

OTHER PUBLICATIONS

Dental Imaging Associates, Inc., "The DIA Anatomic Abutment System™," 12 pages (Oct. 1991).*

(Continued)

*Primary Examiner* — Cris L Rodriguez
*Assistant Examiner* — Heidi M Eide
(74) *Attorney, Agent, or Firm* — Nixon Peabody LLP

(57) ABSTRACT

An implant delivery system includes a carrier that is attached to an implant. The carrier includes a main body having a lower portion to be attached to the implant and an upper portion. The upper portion includes an internally threaded section having a polygonal internal cross-section. The polygonal cross-section engages a tool that applies torque to install the implant into bone. The threaded section receives a threaded portion of a secondary component to be coupled to the carrier after the implant has been installed. One secondary component is a gingival healing component. Thus, the combination of the carrier and the gingival healing component acts as a healing abutment after the carrier has been used to install the implant.

21 Claims, 22 Drawing Sheets

U.S. PATENT DOCUMENTS

| | | | |
|---|---|---|---|
| 4,011,602 A | 3/1977 | Rybicki et al. | 433/173 |
| 4,158,256 A | 6/1979 | Wiland et al. | 32/12 |
| 4,324,549 A | 4/1982 | Madray | 433/169 |
| 4,380,436 A | 4/1983 | Kipp | 433/182 |
| 4,416,629 A | 11/1983 | Mozsary et al. | 433/174 |
| 4,444,310 A | 4/1984 | Odell | 206/366 |
| 4,490,116 A | 12/1984 | Deutsch et al. | 433/215 |
| 4,540,367 A | 9/1985 | Sulc | 433/181 |
| 4,571,185 A | 2/1986 | Rota | 433/173 |
| 4,671,410 A | 6/1987 | Hansson et al. | 206/438 |
| 4,681,542 A | 7/1987 | Baum | 433/172 |
| 4,712,681 A | 12/1987 | Branemark et al. | 206/438 |
| 4,715,817 A | 12/1987 | Zuest et al. | 433/181 |
| 4,722,688 A | 2/1988 | Lonca | 433/173 |
| 4,722,733 A | 2/1988 | Howson | 604/411 |
| 4,744,754 A | 5/1988 | Ross | 433/173 |
| 4,758,161 A | 7/1988 | Niznick | 433/173 |
| 4,763,788 A | 8/1988 | Jorneus et al. | 206/438 |
| 4,824,372 A | 4/1989 | Jorneus et al. | 433/174 |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,648 A | 8/1989 | Krueger | 206/63.5 |
| 4,856,994 A * | 8/1989 | Lazzara et al. | 433/173 |
| 4,906,191 A | 3/1990 | Söderberg | 433/213 |
| 4,955,811 A | 9/1990 | Lazzara et al. | 433/173 |
| 4,978,007 A | 12/1990 | Jacobs et al. | 206/469 |
| 4,988,298 A | 1/1991 | Lazzara et al. | 433/173 |
| 5,006,069 A | 4/1991 | Lazzara et al. | 433/173 |
| 5,015,186 A | 5/1991 | Detsch | 433/173 |
| 5,026,285 A | 6/1991 | Durr et al. | 433/173 |
| 5,030,094 A | 7/1991 | Nardi et al. | 433/169 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,049,072 A | 9/1991 | Lueschen | 433/173 |
| 5,049,073 A | 9/1991 | Lauks | 433/173 |
| 5,062,800 A | 11/1991 | Niznick | 433/229 |
| 5,064,375 A | 11/1991 | Jörnéus | 433/229 |
| 5,069,622 A | 12/1991 | Rangert et al. | 433/173 |
| 5,071,351 A | 12/1991 | Green, Jr. et al. | 433/173 |
| 5,073,111 A | 12/1991 | Daftary | 433/173 |
| 5,100,323 A | 3/1992 | Friedman et al. | 433/173 |
| 5,105,690 A | 4/1992 | Lazzara et al. | 81/436 |
| 5,106,300 A | 4/1992 | Voitik | 433/173 |
| 5,125,840 A | 6/1992 | Durr et al. | 433/173 |
| 5,125,841 A | 6/1992 | Carlsson et al. | 433/213 |
| 5,135,395 A | 8/1992 | Marlin | 433/174 |
| 5,140,877 A | 8/1992 | Sloan | 81/439 |
| 5,145,371 A | 9/1992 | Jorneus | 433/173 |
| 5,145,372 A | 9/1992 | Daftary et al. | 433/173 |
| 5,154,612 A | 10/1992 | Carlsson et al. | 433/173 |
| 5,158,458 A | 10/1992 | Perry | 433/141 |
| 5,180,303 A | 1/1993 | Hornburg et al. | 433/173 |
| 5,188,800 A | 2/1993 | Green, Jr. et al. | 422/23 |
| 5,195,891 A * | 3/1993 | Sulc | 433/173 |
| 5,209,659 A | 5/1993 | Friedman et al. | 433/173 |
| 5,209,666 A | 5/1993 | Balfour et al. | 433/173 |
| 5,211,561 A | 5/1993 | Graub | 433/169 |
| 5,213,502 A | 5/1993 | Daftary | 433/172 |
| 5,238,405 A | 8/1993 | Marlin | 433/173 |
| 5,246,368 A | 9/1993 | Sillard | 433/167 |
| 5,246,370 A | 9/1993 | Coatoam | 433/173 |
| 5,281,140 A | 1/1994 | Niznick | 433/172 |
| 5,292,252 A | 3/1994 | Nickerson et al. | 433/173 |
| 5,297,963 A | 3/1994 | Dafatry | 433/172 |
| 5,312,254 A | 5/1994 | Rosenlicht | 433/173 |
| 5,316,476 A | 5/1994 | Krauser | 433/173 |
| 5,322,443 A | 6/1994 | Beaty | 433/141 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,368,160 A | 11/1994 | Leuschen et al. | 206/339 |
| 5,368,483 A | 11/1994 | Sutter et al. | 433/173 |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,437,550 A | 8/1995 | Beaty et al. | 433/141 |
| 5,437,551 A | 8/1995 | Chalifoux | 433/173 |
| 5,462,436 A | 10/1995 | Beaty | 433/141 |
| 5,476,383 A | 12/1995 | Beaty et al. | 433/214 |
| 5,489,210 A | 2/1996 | Hanosh | 433/173 |
| 5,492,471 A | 2/1996 | Singer | 433/172 |
| 5,527,182 A | 6/1996 | Willoughby | 433/172 |
| 5,538,426 A | 7/1996 | Harding et al. | 433/172 |
| 5,538,428 A | 7/1996 | Staubli | 433/173 |
| 5,556,280 A | 9/1996 | Pelak | 433/172 |
| 5,564,921 A | 10/1996 | Marlin | 433/172 |
| 5,564,924 A | 10/1996 | Kwan | 433/173 |
| 5,582,299 A | 12/1996 | Lazzara et al. | 206/63.5 |
| 5,591,029 A | 1/1997 | Zuest | 433/173 |
| 5,626,227 A | 5/1997 | Wagner et al. | 206/369 |
| 5,630,717 A | 5/1997 | Zuest et al. | 433/172 |
| 5,651,675 A | 7/1997 | Singer | 433/172 |
| 5,658,147 A | 8/1997 | Phimmasone | 433/213 |
| 5,662,476 A | 9/1997 | Ingber et al. | 433/213 |
| 5,674,069 A | 10/1997 | Osorio | 433/172 |
| 5,674,071 A | 10/1997 | Beaty et al. | 433/172 |
| 5,674,073 A | 10/1997 | Ingber et al. | 433/213 |
| 5,681,167 A | 10/1997 | Lazarof | 433/174 |
| 5,685,715 A | 11/1997 | Beaty et al. | 433/173 |
| 5,688,123 A | 11/1997 | Meiers et al. | 433/173 |
| 5,692,904 A | 12/1997 | Beaty et al. | 433/141 |
| 5,704,788 A | 1/1998 | Milne | 433/173 |
| 5,733,123 A | 3/1998 | Blacklock et al. | 433/173 |
| 5,759,036 A | 6/1998 | Hinds | 433/214 |
| 5,762,500 A | 6/1998 | Lazarof | 433/213 |
| 5,829,981 A | 11/1998 | Ziegler | 433/214 |
| 5,871,358 A | 2/1999 | Ingber et al. | 433/213 |
| 5,873,720 A * | 2/1999 | Jorneus et al. | 433/172 |
| 5,888,218 A | 3/1999 | Folsom | 623/16 |
| 5,897,320 A | 4/1999 | Gittleman | 433/180 |
| 5,904,483 A | 5/1999 | Wade | 433/173 |
| 5,938,443 A | 8/1999 | Lazzara et al. | 433/173 |
| 5,947,736 A | 9/1999 | Behrend | 433/214 |
| 5,964,591 A | 10/1999 | Beaty et al. | 433/173 |
| 6,012,923 A | 1/2000 | Bassett et al. | 433/172 |
| 6,030,219 A | 2/2000 | Zuest et al. | 433/181 |
| 6,068,478 A | 5/2000 | Grande et al. | 433/172 |
| 6,099,311 A | 8/2000 | Wagner et al. | 433/163 |
| 6,159,008 A | 12/2000 | Kumar | 433/141 |
| 6,203,323 B1 | 3/2001 | Beaty et al. | 433/173 |
| 6,290,499 B1 | 9/2001 | Lazzara et al. | 433/173 |
| 6,382,977 B1 | 5/2002 | Kumar | 433/214 |

FOREIGN PATENT DOCUMENTS

| | | |
|---|---|---|
| WO | WO 96/29019 | 9/1996 |
| WO | WO 98/52490 | 11/1998 |
| WO | WO 00/02497 | 1/2000 |

OTHER PUBLICATIONS

Lewis, Steven G., et al., "Single Tooth Implant Supported Restorations," The International Journal of Oral & Maxillofacial Implants, vol. 3, No. 1, pp. 25-30 (1988).*

Lewis, S., et al., "The 'UCLA' Abutment," The International Journal of Oral & Maxillofacial Implants, vol. 3, No. 3, pp. 183-189 (1988).*

Perri, George, et al., "Single Tooth Implants," CDA Journal, vol. 17, No. 3, pp. 30-33 (Mar. 1989).

Zarb, George A., et al., "Tissue-Integrated Prostheses—Osseointegration in Clinical Dentistry," Quintessence Publishing Co., Inc., Chapter 17, pp. cover, 293-315 (1985).

* cited by examiner

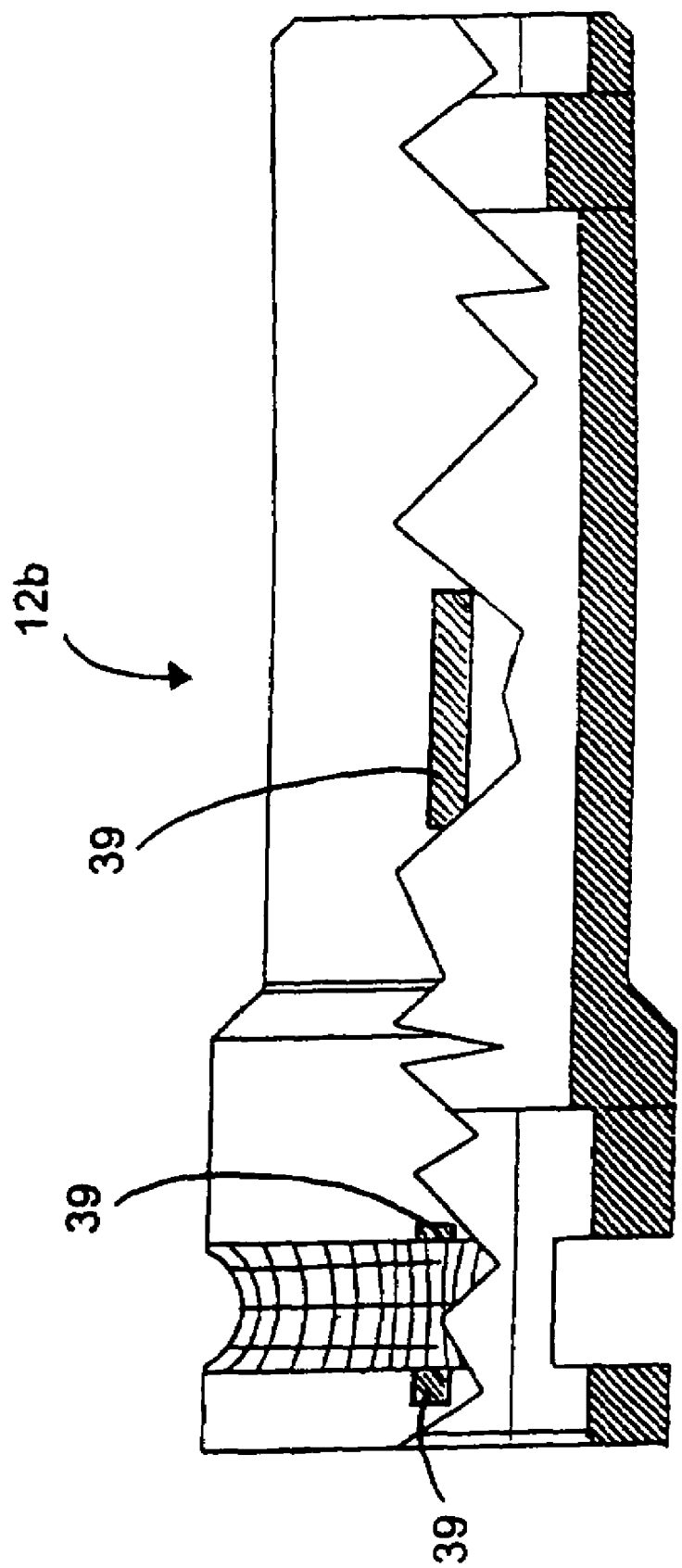

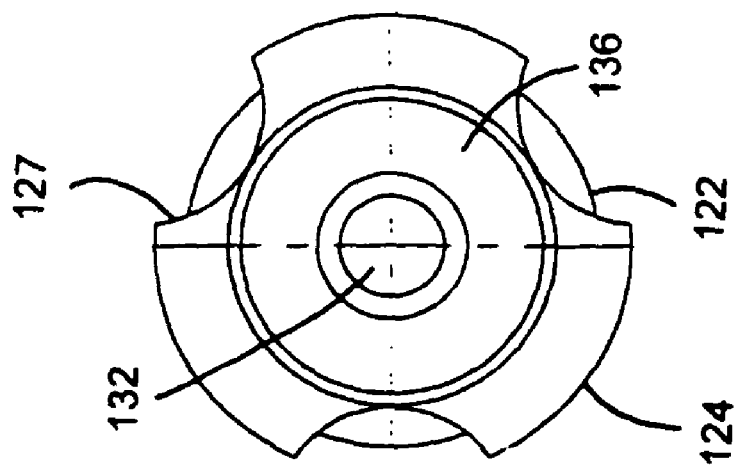
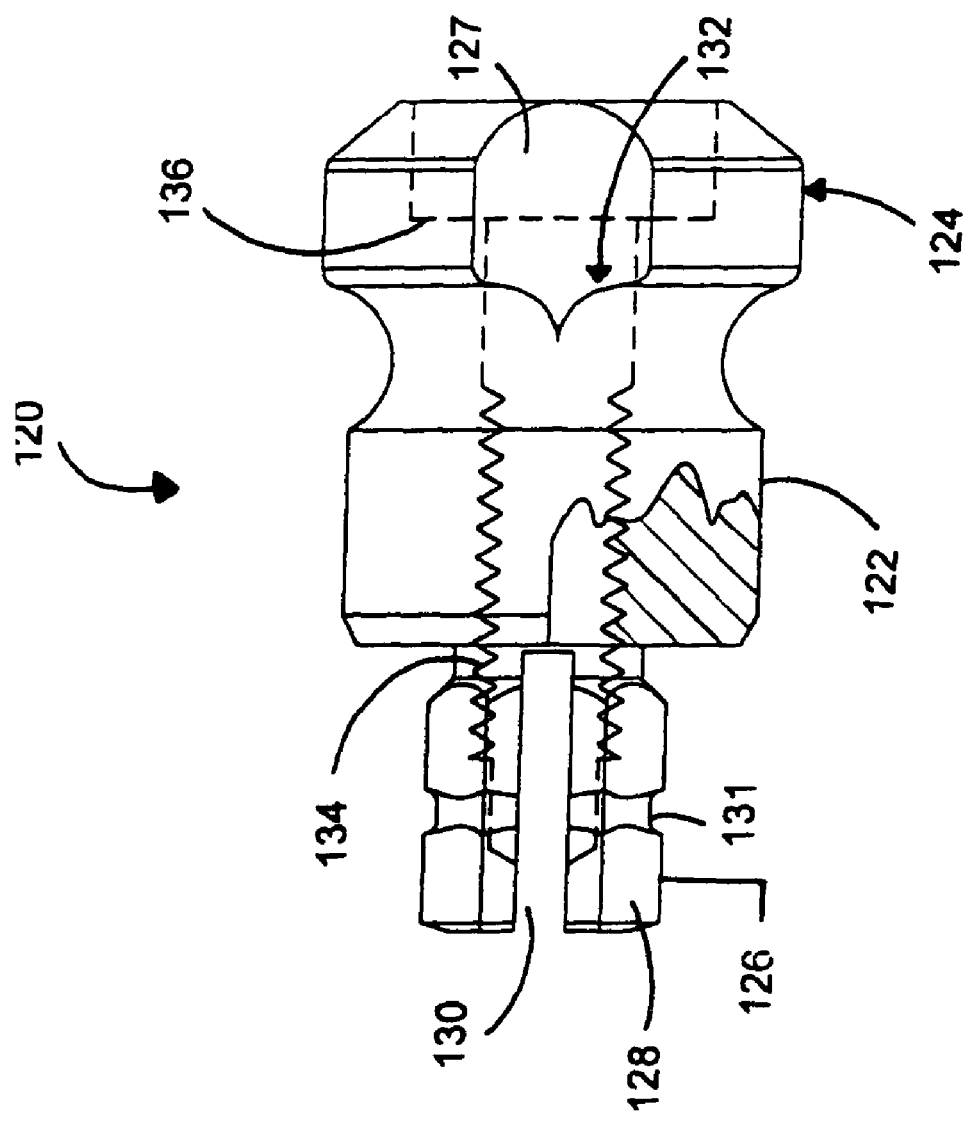
Fig. 8b
Fig. 8a

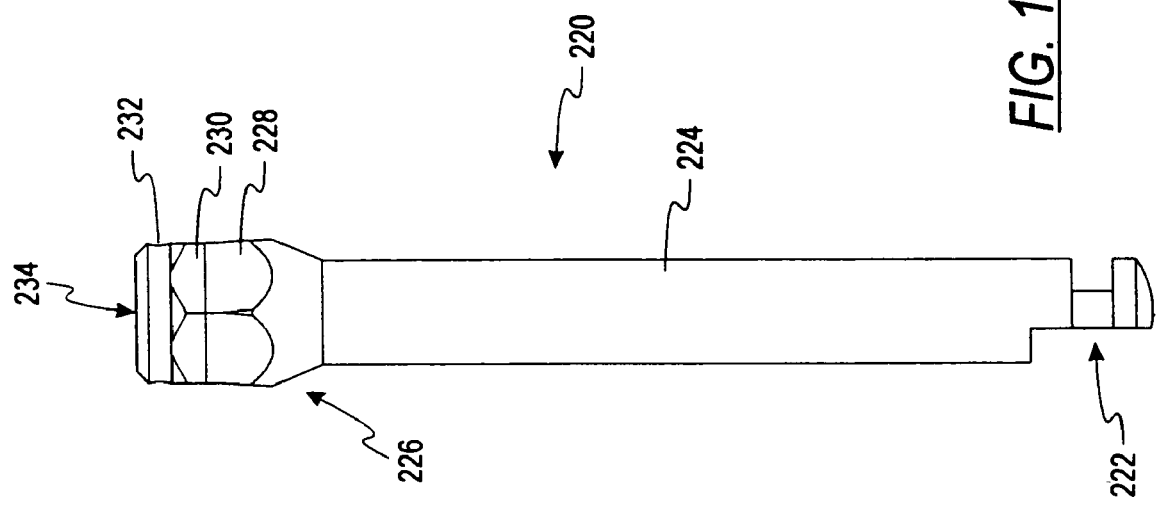
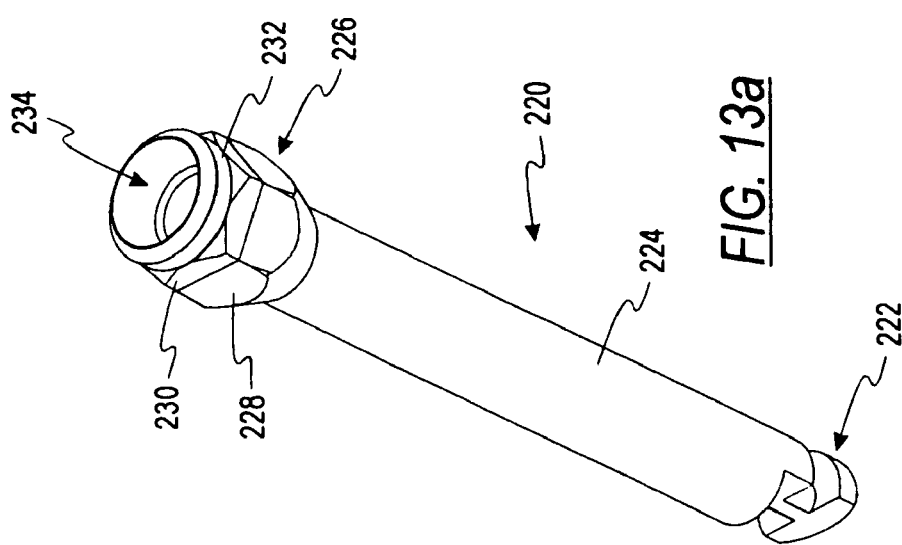

IMPLANT DELIVERY SYSTEM

RELATED APPLICATIONS

This application is a divisional of application Ser. No. 10/641,389, filed Aug. 14, 2003, and issued as U.S. Pat. No. 7,344,376 on Mar. 18, 2008, entitled "Implant Delivery System", which is a divisional of application Ser. No. 09/812,161, filed Mar. 19, 2001, and issued as U.S. Pat. No. 6,619,958 on Sep. 16, 2003, entitled "Implant Delivery System"; which is a continuation-in-part of application Ser. No. 09/416,221, filed Oct. 12, 1999, and issued as U.S. Pat. No. 6,203,323 on Mar. 20, 2001, entitled "Implant Delivery System"; which is a continuation of application Ser. No. 09/057,087, filed Apr. 8, 1998, and issued as U.S. Pat. No. 5,964,591 on Oct. 12, 1999, entitled "Implant Delivery System"; which claimed the benefit of priority of Application No. 60/043,131, filed Apr. 9, 1997, entitled "Implant Delivery System."

FIELD OF THE INVENTION

The invention relates to a system and a technique for delivering and installing an implant in living bone. Specifically, the system includes an implant and a carrier attached thereto that are packaged together and delivered to the installation site within the living bone. The system also includes a variety of tools that provide flexibility in the installation process and additional components that permit the taking of impressions during first stage surgery.

BACKGROUND OF THE INVENTION

It is known to enclose sterilized dental implants in packages that will preserve sterility until opened. The packages are delivered to the clinician, who elects when and where to open the package. It is also known to include in such packages carrier devices attached to the implants which enable the implant to be manipulated without directly touching it.

Placing a dental implant in the jawbone of a patient is typically the beginning of several procedures which have been developed for providing implant-supported dentition. All procedures use components, frequently referred to as an "impression coping," for transferring to the dental laboratory information about the patient's mouth in the area of the implant on which the dentition is to be supported. Until fairly recently, it has been the usual practice to delay this information transfer step several months after installing the implant to allow the implant to "osseointegrate" with the host bone. The result is a two stage surgical procedure; the first stage includes the installation of the implant; the second stage involves another surgery in which the gum tissue is reopened and an impression coping is fitted to the implant to gather the needed information. Since laboratory procedures cannot begin without this information, the development of a patient's dental prosthesis was generally delayed about three to six months while the osseointegration process occurred.

Generally, the carrier has a non-rotational engagement surface (i.e., non-circular) that a dental tool engages. When the implant has external threads, the dental tool is rotated such that the rotation imparted on the combination of the carrier and the implant screws the implant into the jawbone. In some situations, however, it is necessary to have a longer carrier because the gingiva above the jawbone is thick, such that only a smaller portion of the carrier is exposed through the gingiva. In that situation, clinicians often remove the standard carrier from the implant and install onto the implant a longer carrier to accommodate the thicker gingiva. Any time the clinician touches the implant, however, there is a risk that the sterile surfaces on the implant may become contaminated.

Recently, a protocol was developed which includes taking an impression of the patient's mouth during first stage surgery. Immediately after the implant has been installed into its final position at the site of the jawbone, the clinician removes the carrier from the implant and installs onto the implant an impression coping. Once the impression coping is installed on the implant, the clinician then applies impression material to the region to take the impression of the site in the patient's mouth. The impression would then allow for the development of a temporary, or possibly, a permanent dentition that would be attached to the implant after osseointegration. One of the problems associated with this new protocol is the potential for movement of the implant, which has been accurately placed into the patient's jawbone, caused by the attachment of the impression coping.

SUMMARY OF THE INVENTION

The present invention provides for an implant delivery system that includes an implant, a carrier, and an implant screw attaching the implant to the carrier. The implant can be of a variety of types and typically includes an internally threaded bore extending along its central axis. The carrier has a through bore extending entirely therethrough in which the implant screw resides. The implant screw connects the implant to the carrier such that the lower surface of the carrier abuts the upper surface of the implant. A pair of non-circular fittings on the implant and carrier lock these two components against rotation relative to one another.

The through bore of the carrier includes a non-circular socket that is to be engaged by a correspondingly-shaped section of a coupling tool. The coupling tool is engaged by a device which imparts movement on the combination of the implant and the carrier that is necessary to install the implant into its final position within the jawbone. When the implant includes an externally threaded body, the device may be a dental handpiece that imparts rotational movement on the implant to screw it into the bone. The coupling tool can be made in a variety of lengths such that the clinician selects the appropriate length for the prevailing conditions in the patient's mouth.

After the implant is installed in its final position, the carrier is removed through the use of a driver. The driver includes a surface which the clinician grasps, a shank extending from the grasping surface, and a guide that is connected to the shank. The guide is free to move rotationally around the shank, but is limited in its axial movement along the shank. The lower end of the shank includes a surface which is non-rotationally coupled to the implant screw. The guide includes at its lower end an engaging portion which is to be non-rotationally engaged within the socket of the carrier. During removal of the implant screw, the engaging portion of the guide is coupled to the internal socket of the carrier and the lower end of the shank is engaged within a driver socket in the implant screw. When the clinician rotates the grasping surface, the carrier is held steady on the implant while the implant screw is rotated, such that it releases the carrier from the implant. Due to the configuration of the driver, the carrier can be removed from the implant without imparting any motion whatsoever on the carrier and, therefore, the implant.

If the clinician so desires, he or she can also utilize the combination of the implant and the carrier to take an impression of the patient's mouth during first stage surgery. An impression coping and its associated bolt can be affixed into the socket of the carrier. The impression coping has at its lower end an expandable non-rotational boss that fits within the carrier's socket. When the bolt is threaded into an internally threaded bore within the impression coping, the boss expands outward such that it becomes press fit into the socket of the carrier. This press fit engagement provides enough retention force so that an impression can be made by the clinician without the risk of the impression coping loosening from the carrier.

The bolt associated with the impression components can include an elongated head so that the bolt and impression component act as a "pick-up"-type impression coping. Alternatively, a short-headed bolt can be used so that the bolt and impression component act as a "transfer"-type impression coping. In either case, after the impression is taken, the carrier is reattached to the impression coping using the bolt. The combination of the carrier and impression coping is then used with the impression material in the dental laboratory to develop a prosthetic tooth for the patient.

Regardless of whether the clinician chooses to take an impression of the region during first stage surgery, he or she must cover the internally threaded bore of the implant after the carrier is removed. Thus, the combination of the implant carrier and implant screw is typically packaged with a healing cap. The healing cap mates with the internally threaded bore of the implant and is placed thereon prior to suturing the gingiva.

In another embodiment, the carrier includes an internal polygonal section that is at least partially defined by a threaded surface. The threaded surface includes one or more threads making a plurality of turns on the internal portion of the carrier. While the polygonal section serves the same purpose as the non-circular socket of the previously described carrier, the threaded surface provides a structure to which various secondary components can be attached. For example, the carrier can be converted into a gingival healing abutment by the addition of a gingival healing component that screws into the threaded surface. Such a gingival component can simply be a screw that has a head that is large enough to seal the opening in the carrier, or can be a sleeve-type component that fits around the outer periphery of the carrier.

BRIEF DESCRIPTION OF THE DRAWINGS

The foregoing and other advantages of the invention will become apparent upon reading the following detailed description and upon reference to the drawings.

FIGS. 2a-2c illustrate a series of carriers having various lengths.

FIGS. 8a-8b illustrate an impression coping that can be attached to the carrier of the present invention.

FIGS. 13a-13b illustrate a tool used with the implant delivery system of FIG. 12.

Figure 1B:
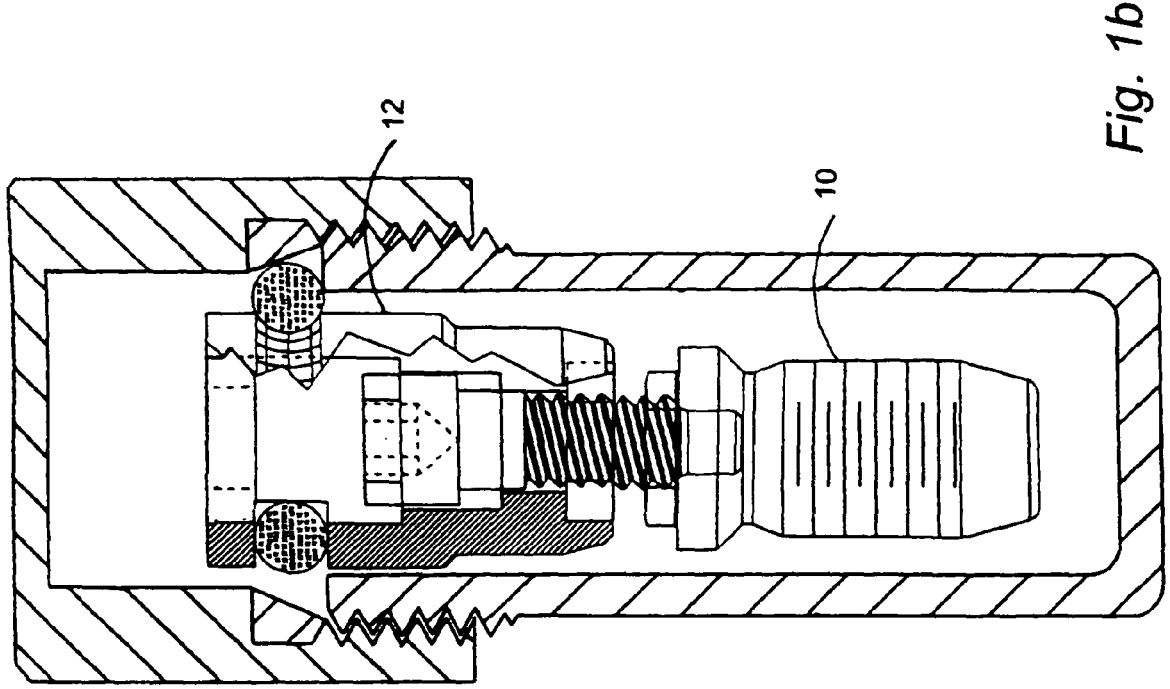
FIG. 1b illustrates the implant, carrier, and implant screw within a package.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Figure 1A:
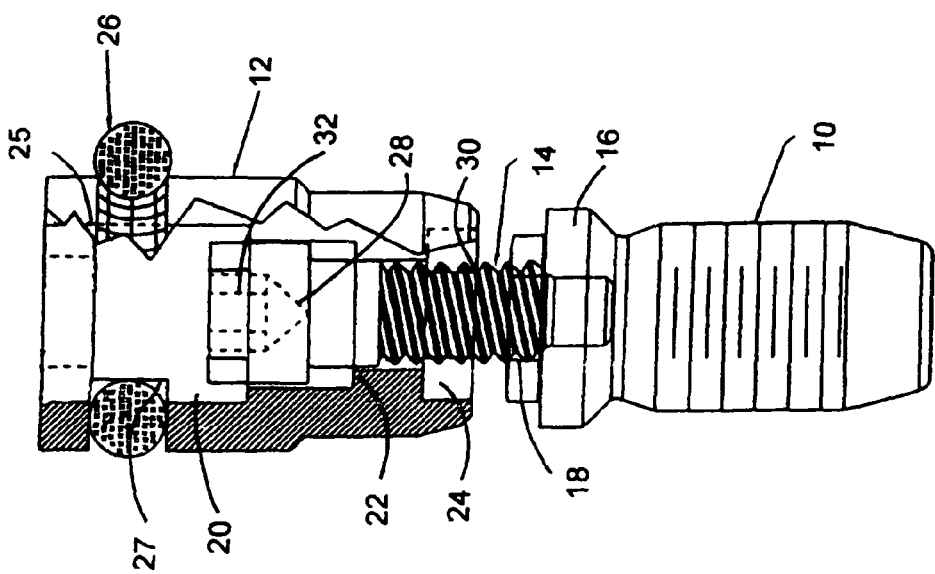
FIG. 1a illustrates an implant, a carrier, and an implant screw holding the carrier to the implant.

Referring initially to FIG. 1a, an implant 10 is attached to a carrier 12 with an implant screw 14. The implant 10 includes a non-circular manipulating fitting 16 which, as shown, is in the shape of a hexagon. Extending into the upper region of the implant 10 and through the manipulating fitting 16 is a threaded bore 18.

The carrier 12 has a through bore 20 extending from its upper end to its lower end. The through bore 20 has various sections. A shoulder 22 is positioned within the through bore 20 near the lower end of the carrier 12. Also located at the lower end of the through bore 20 is an implant socket 24 that is configured to mate with the manipulating fitting 16 of the implant 10. At the upper end of the carrier 12 is another socket 25 which, as described below, engages the guide portion of the driver and also may receive a mounting section of an impression coping. The socket 25 includes a non-circular internal surface (usually hexagonal) for non-rotational engagement with the driver and the coping.

An O-ring 26 is positioned within a groove 27 on the exterior surface of the carrier 12. Typically, the O-ring 26 is a polymer or an elastomer so that it is somewhat resilient. As shown in FIG. 1b, the O-ring 26 engages a ledge within a package containing the combination of the implant 10 and the carrier 12 such that only the O-ring 26 contacts the package. Consequently, the carrier 12 and the implant 10 are suspended in the package away from the walls so that the likelihood that either the implant 10 or the carrier 12 will become contaminated is greatly reduced. One type of suitable packaging arrangement is disclosed in U.S. Pat. No. 5,582,299 entitled "Dental Implant Packaging," which is herein incorporated by reference in its entirety.

Furthermore, the groove 27 does not have an entirely circular cross-section, as can be seen in FIG. 1a by the fact that the O-ring 26 is not centered on the central axis of the carrier 12. Instead, the groove 27 includes a region that is cut into the carrier 12 such that the cut section enters the socket 25. In other words, the groove 27 includes a hole which allows access into the socket 25. Consequently, the O-ring 26 includes a portion that rests within the socket 25 which, as will be described below, assists in retaining tools within the socket 25.

The implant screw 14 includes a head 28 that engages the shoulder 22 of the carrier 12. The implant screw 14 also includes a threaded shaft 30 which threadably engages the threaded bore 18 of the implant 10. Thus, after manufacturing the implant 10 and the carrier 12, and prior to packaging these two components, the manufacturer attaches these two components by use of the implant screw 14. In its final position (not shown), the implant screw 14 forces the lower end of the carrier 12 into contact with the upper surface of the implant 10 as the implant socket 24 envelops over the manipulating fitting 16 of the implant 10.

The implant screw 14 also includes within its head 28 a driver socket 32. The driver socket 32 is engaged by the driver tool which attaches the implant screw 14 to or removes the implant screw 14 from the assembly. When the implant screw 14 is removed, the carrier 12 can be released from the implant 10.

Because of the size of the implant screw 14, it is difficult to handle, especially when doing so in a patient's mouth. Consequently, after the implant screw 14 is placed within the through bore 20 to attach the implant 10 to the carrier 12, the O-ring 26 is inserted within the groove 27 such that a portion of the O-ring 26 enters the through bore 20 in the area of the socket 25. The O-ring 26 protrudes inward towards the central axis of the carrier 12 far enough to reduce the effective diameter of the through bore 20 to a dimension that is less than the dimension of the head of the implant screw 14. Thus, the implant screw 14 is held captive in the carrier 12 between the O-ring 26 and the shoulder 22. Alternatively, the through bore 20 of the carrier 12 can be manufactured in a manner which causes an irregularity on its surface after the implant screw 14 is placed therein to effectuate the captivity of the implant screw 14.

Figure 2C:
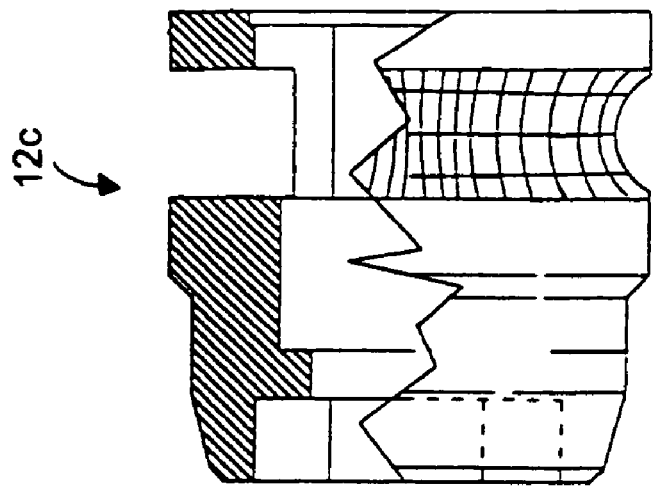
Figure 2A:
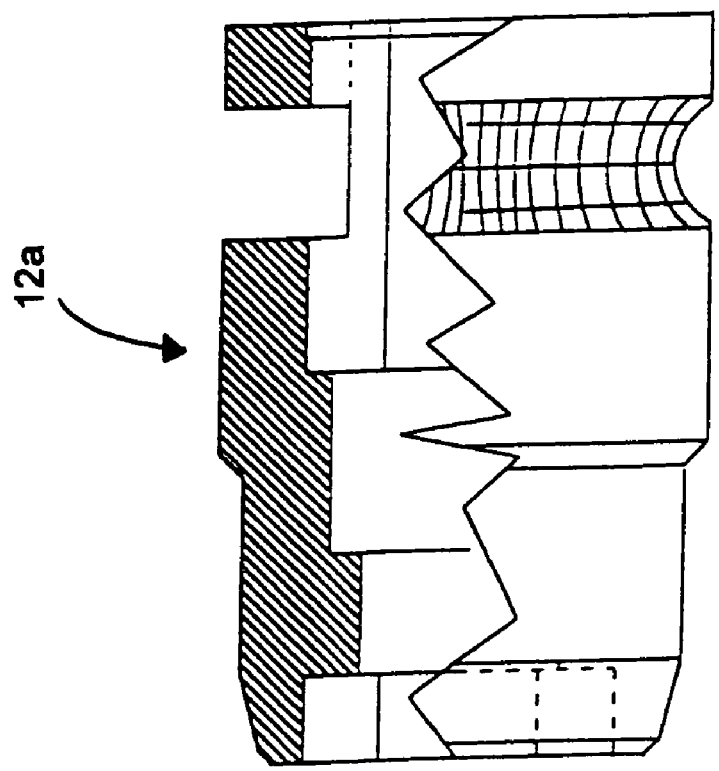

Depending on the conditions in the patient's mouth, the implant size is selected by the clinician that best suits the patient's condition. To assist the clinician with installing the implant properly, the carrier 12 is manufactured in various lengths, as shown in FIGS. 2a-2c. In FIG. 2a, the carrier 12a, which includes all of the elements of the carrier 12 shown in FIG. 1, is of an average length. In FIG. 2b, the carrier 12b is of a long length. Again, the carrier 12b includes all of the elements of the carrier 12 in FIG. 1 and also includes reference markings 39. These markings 39 are aligned with the faces of the implant socket 24. Thus, when inserting the carrier 12 and the implant 10 into the bone, the clinician can visualize the orientation of the faces of the manipulating fitting 16 relative to the jawbone through the use of these markings 39.

In FIG. 2c, the carrier 12c is of a short length, but contains all of the elements of the carrier 12 in FIG. 1. Because of the variety of lengths in which the carrier 12 can be manufactured, the manufacturer chooses a carrier length that functions the best with the implant to which the carrier 12 is attached. As an example of the carrier sizes, the carrier 12a may be approximately 7.5 mm, the carrier 12b about 15 mm, and the carrier 12c about 5.0 mm. The width of each carrier 12a, 12b, and 12c is about 5 mm.

Figure 3A:
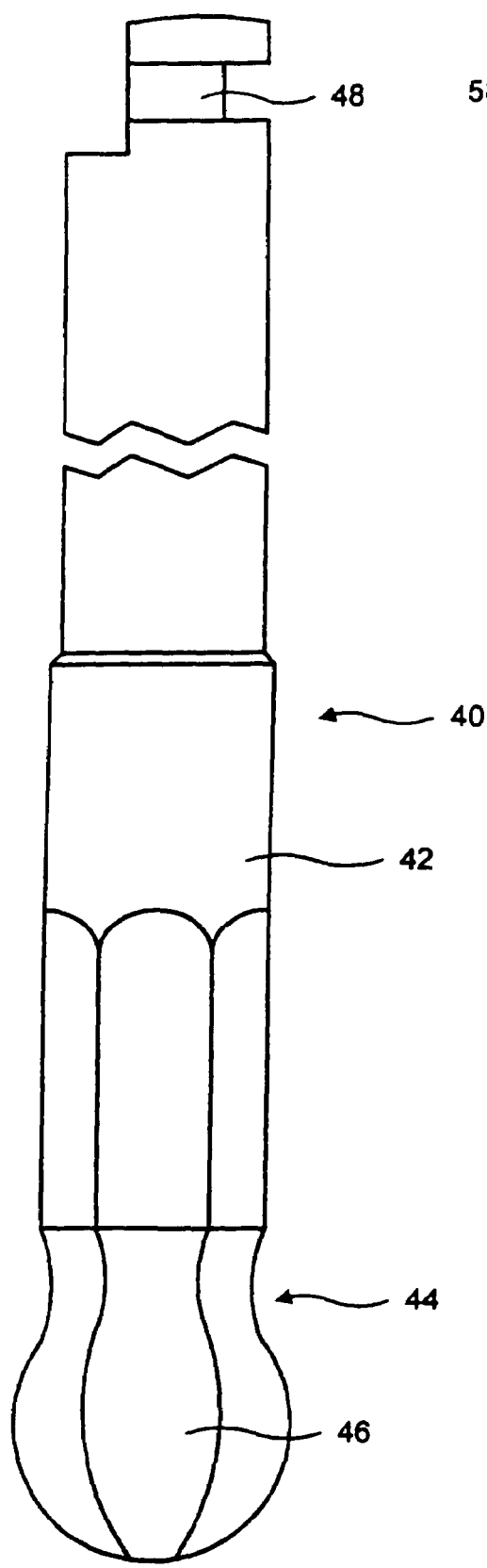
FIGS. 3a-3b illustrate two types of coupling tools that can impart rotational movement on the combination of the implant and the carrier.
Figure 3B:
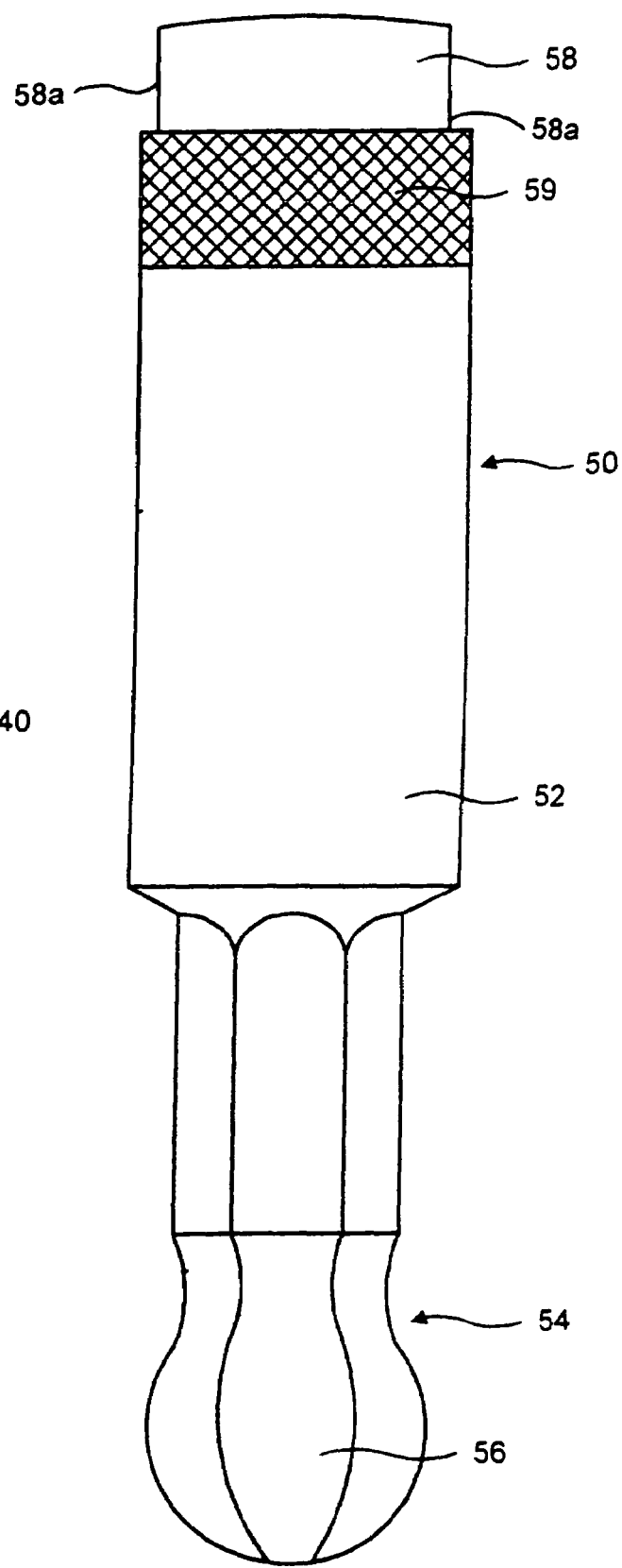

FIGS. 3a and 3b illustrate tools that engage the combination of the implant 10 and the carrier 12 to install the implant 10 within the jawbone. In FIG. 3a, a tool 40 includes a shaft 42 having at its lower end a ball hex fitting 44. The ball hex fitting 44 has six surfaces 46 positioned circumferentially around the fitting 44. The upper end of the shaft 42 includes a connecting arrangement 48 that allows the tool 40 to be coupled to a power driver such as a common dental handpiece. Thus, as the power driver operates, the tool 40 rotates and imparts rotational movement on the carrier 12 and the implant 10. A cross-section of the ball hex fitting 44 at its maximum diameter has approximately the same cross-section of the socket 25 in the carrier 12.

In FIG. 3b, an alternative tool 50 is illustrated. The tool 50 includes a shaft 52 having at its lower end a ball hex fitting 54. The ball hex fitting 54 includes six surfaces 56 positioned circumferentially therearound. The upper end of the tool 50 has flat engagement surfaces 58 which meet at corners 58a. The flat engagement surfaces 58 (shown here as four flat surfaces) engage a manual rotating mechanism such as a dental wrench. Also located at the upper portion of the tool 50 is a knurled surface 59 which the clinician grasps when initially rotating the combination of the implant 10 and the carrier 12 into the site of the jawbone. Again, a cross-section of the ball hex fitting 54 at its maximum diameter should have approximately the same cross-section of the socket 25 in the carrier 12. Thus, the tool 50 differs from the tool 40 in that the tool 50 is designed for installing the implant 10 into its final position within the jawbone through non-power driven means.

In operation, the clinician selects the tool 40 or 50 that is best suited for the conditions in the patient's mouth. For example, if the clinician knows that the implant 10 will be installed through dense bone, then additional torque is needed. Thus, the clinician will likely choose the tool 40 which can be engaged by a power driver. Alternatively, if the clinician understands the bone tissue in which the implant 10 will be installed in cancellous bone, the clinician may instead choose the tool 50 and not utilize a power driver.

In any event, after choosing the tool 40 or 50 that is best suited for the patient's conditions, the clinician grasps the upper end of the tool 40 or 50 and inserts the ball hex fitting 44 or 54 into the socket 25 of the carrier 12. Consequently, the tools 40 and 50 are devices that can be used by the clinician to transport the combination of the implant 10 and the carrier 12 from its package to the site in the patient's mouth. The portion of the O-ring 26 which extends into the socket 25 assists in retaining the ball hex fitting 44 or 54 within the socket 25. Preferably, the O-ring 26 reduces the effective diameter of the socket 25 to a dimension which is less than the maximum dimension of the ball hex fitting 44 or 54. Once the ball hex fitting 44 is inserted into the socket 25 and past the flexible O-ring 26, the combination of the carrier 12 and the implant 10 can be transported by the tool 40 or 50.

Alternatively, the clinician may feel more comfortable using the wider tool 50 having the knurled surface 59, and choose to use the tool 50 to transport the combination of the implant 10 and the carrier 12 from its package to the installation site. Then, the clinician may replace the tool 50 with the tool 40 and utilize the power driver which rotates the tool 40. In this alternative methodology, utilization of the tool 50 may allow the clinician the ability to start the implant 10 into the jawbone by rotating the tool 50 with his or her fingers.

The tools 40 and 50 can be made in various lengths. Therefore, the clinician no longer needs to substitute the packaged carrier for a longer or shorter carrier to suit the conditions in the patient's mouth, as has been the case in many prior art systems. Instead, the clinician simply chooses the length of the tool 40 or 50 that will best assist him or her in the installation process.

Figure 4:
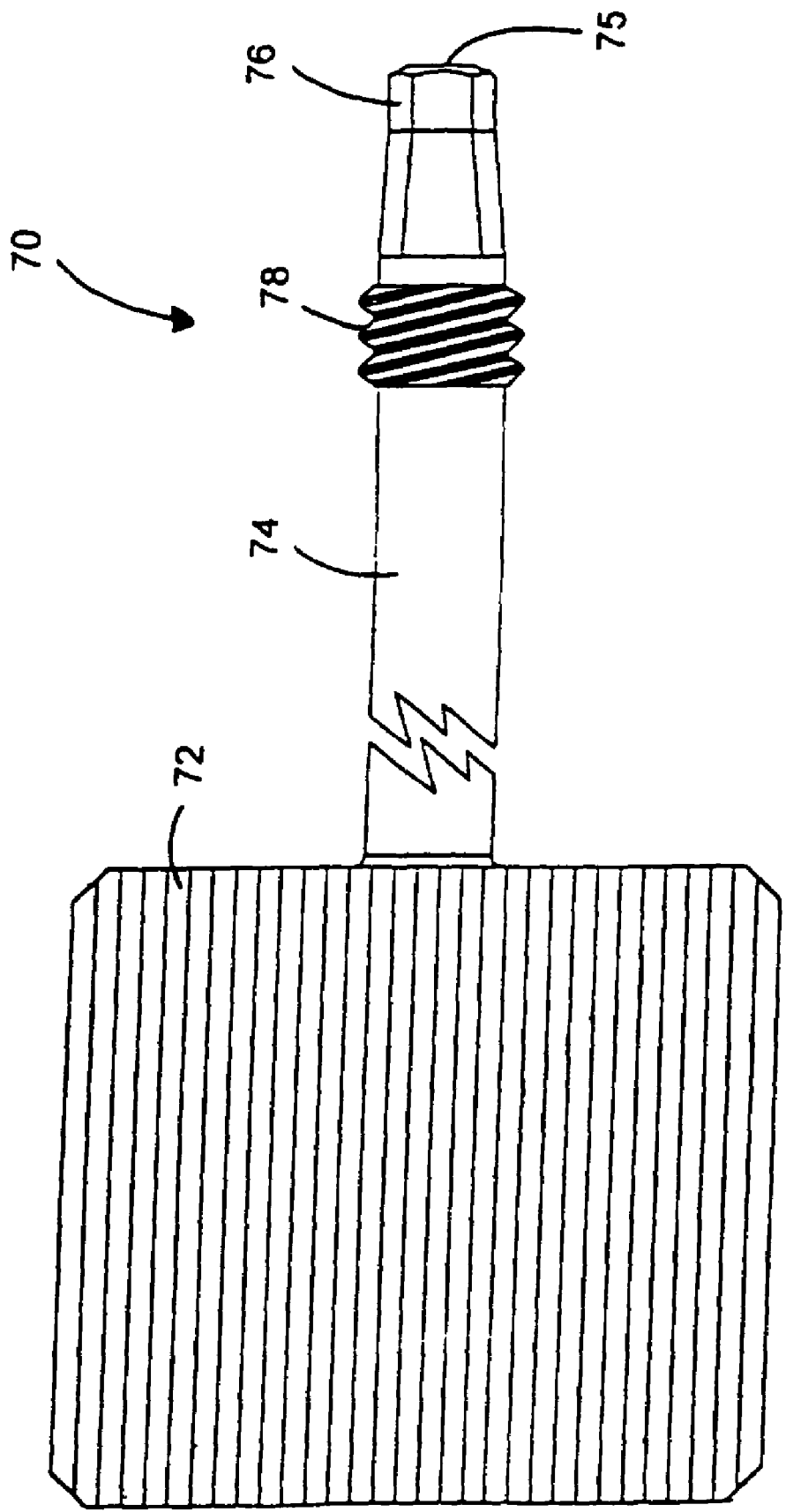
FIG. 4 illustrates a driver that is used to engage and disengage the implant screw.

Referring now to FIG. 4, a driver 70 for use in removing the carrier 12 from and attaching the carrier 12 to the implant 10 is illustrated. The driver 70 includes a head portion 72 which the clinician grasps with his or her fingers. Below the head portion 72 is a shank 74 that extends downward to a lower end 75. Adjacent the lower end is a fitting 76 having a plurality of sides which fits within the driver socket 32 of the implant screw 14 (FIG. 1). The fitting 76 expands outward along the shank 74 from the lower end 75 toward the head 72. This allows for easy insertion of the lower end 75 and fitting 76 into the corresponding driver socket 32 of the implant screw 14. Furthermore, the angled section of the fitting 76 allows for a tight, press-fit engagement of the driver 70 in the driver socket 32 of the implant screw 14. The details of this angled configuration of the driver 70 are disclosed in U.S. Pat. No. 5,105,690 entitled "Manipulator-Driver For Holding And Driving A Screw-Type Article," which is incorporated herein by reference. Additionally, the shank 74 includes a threaded portion 78 which retains a guide thereon, as described below with reference to FIGS. 5 and 6.

Figures 5A, 5B:
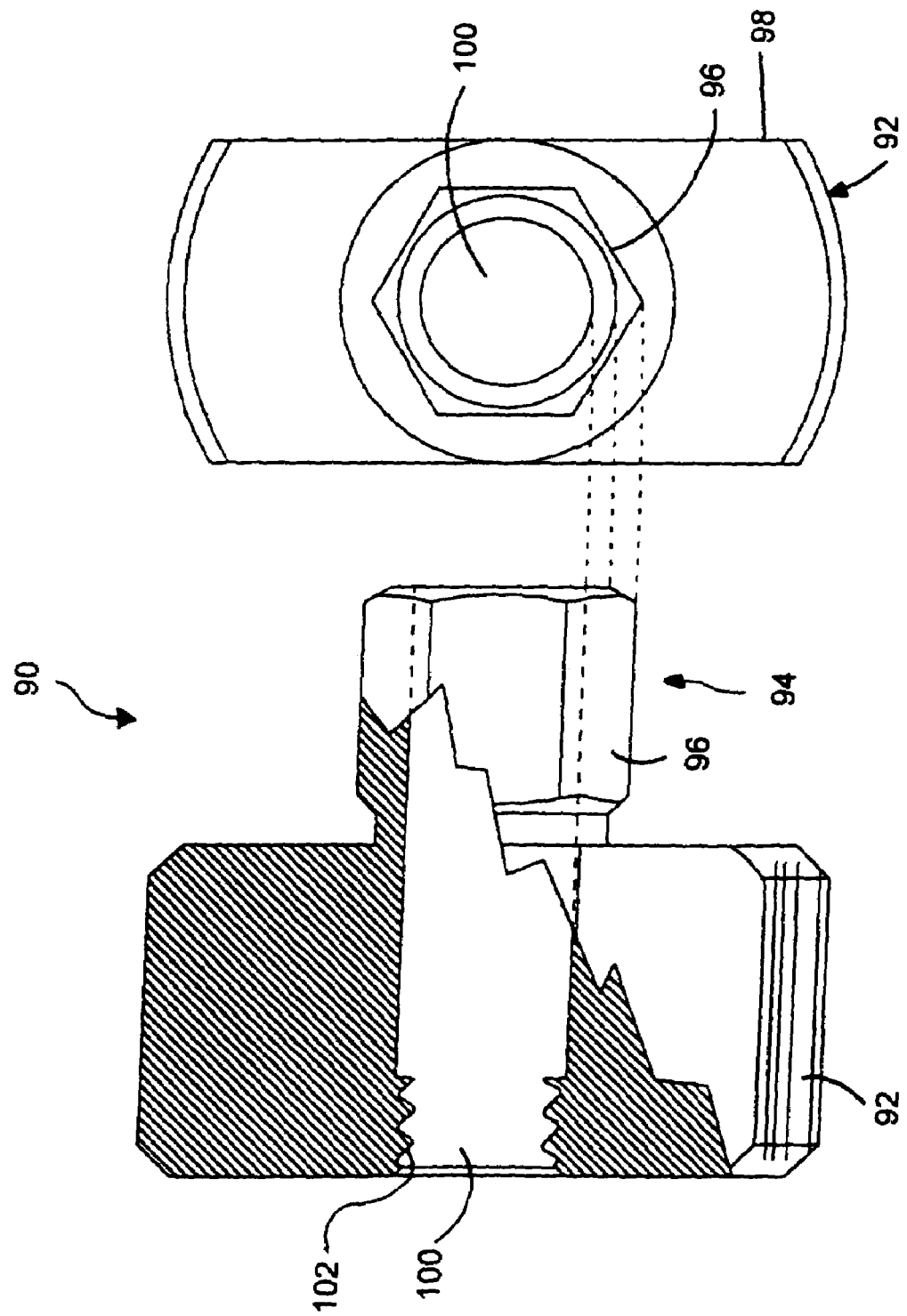
FIGS. 5a-5b illustrate a guide that is used in conjunction with the driver in FIG. 4 to hold the carrier against rotation while manipulating the implant screw.

FIGS. 5*a* and 5*b* are partially broken away side and bottom views, respectively, of a guide 90 that is used in conjunction with the driver 70 of FIG. 4. The guide 90 includes a main body 92 at one end and an engaging portion 94 at the other end. The main body 92 may have a surface which is knurled to allow the clinician a region for grasping. The engaging portion 94 includes a plurality of side surfaces 96 which give the engaging portion 94 a non-circular cross-sectional shape (e.g., hexagonal as shown). As can be best seen in FIG. 5*b*, main body 92 includes two opposing flats 98 which, as described below, provide surfaces which a tool such as a wrench may engage.

Extending through the main body 92 and the engaging portion 94 of the guide 90 is a hole 100. The hole 100 includes a threaded region 102 which matches the thread type of threaded portion 78 on driver 70. As is shown in FIG. 7, the threaded region 102 permits the guide 90 to be retained on the shank 74 of driver 70, thereby reducing the risk that the guide 90 will become detached therefrom.

Figure 6:
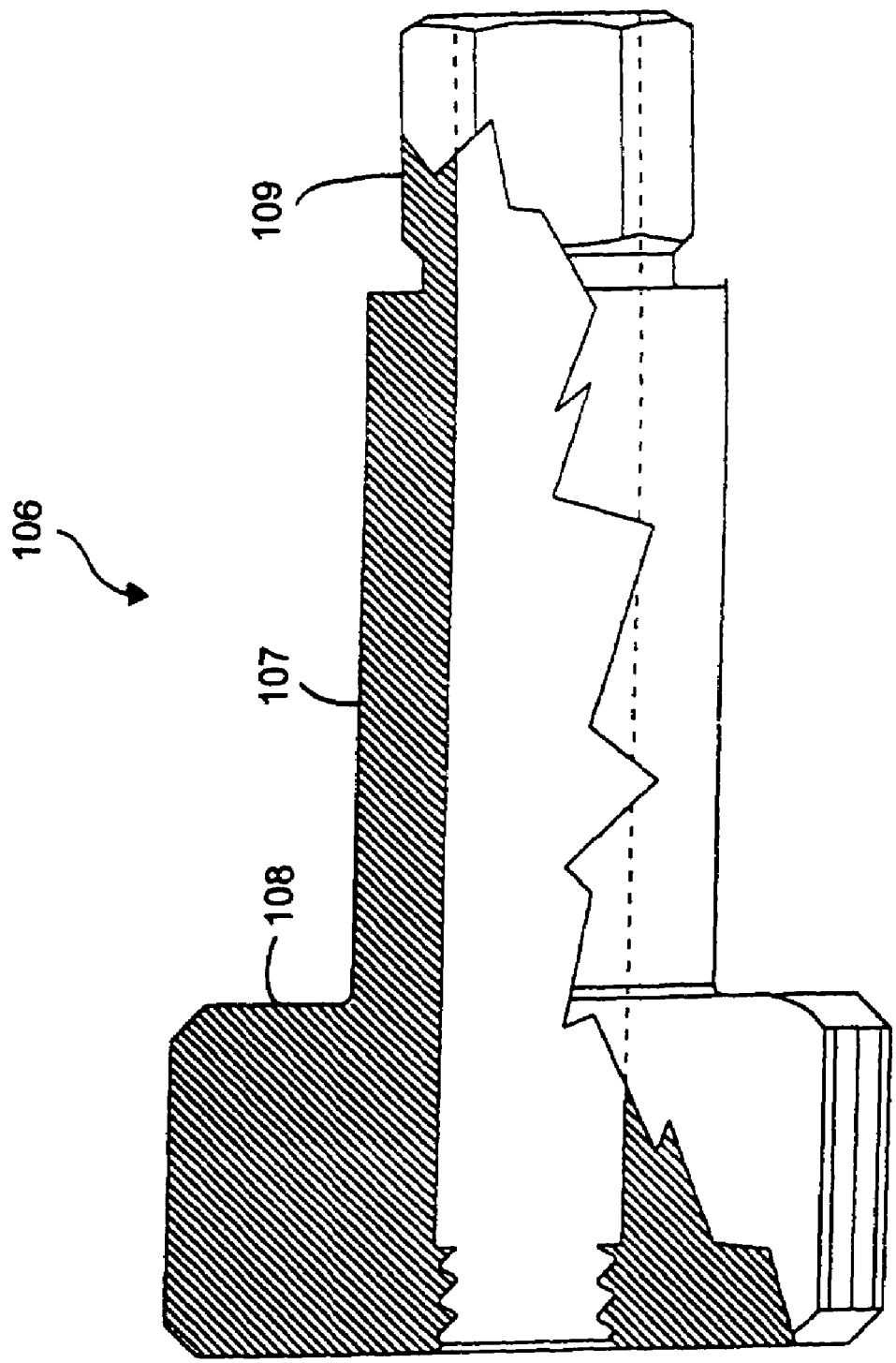
FIG. 6 illustrates an alternative guide similar to the one illustrated in FIGS. 5a-5b.

FIG. 6 is a partially broken away side view of an alternative guide 106 that is similar to the guide 90 in FIGS. 5*a* and 5*b*. The guide 106 of FIG. 6, however, also includes an extended shaft 107 separating the main body 108 from the engaging portion 109. Thus, the guides may be manufactured in a variety of lengths, and the clinician can choose the guide that best suits the needs of the patient.

Figure 7:
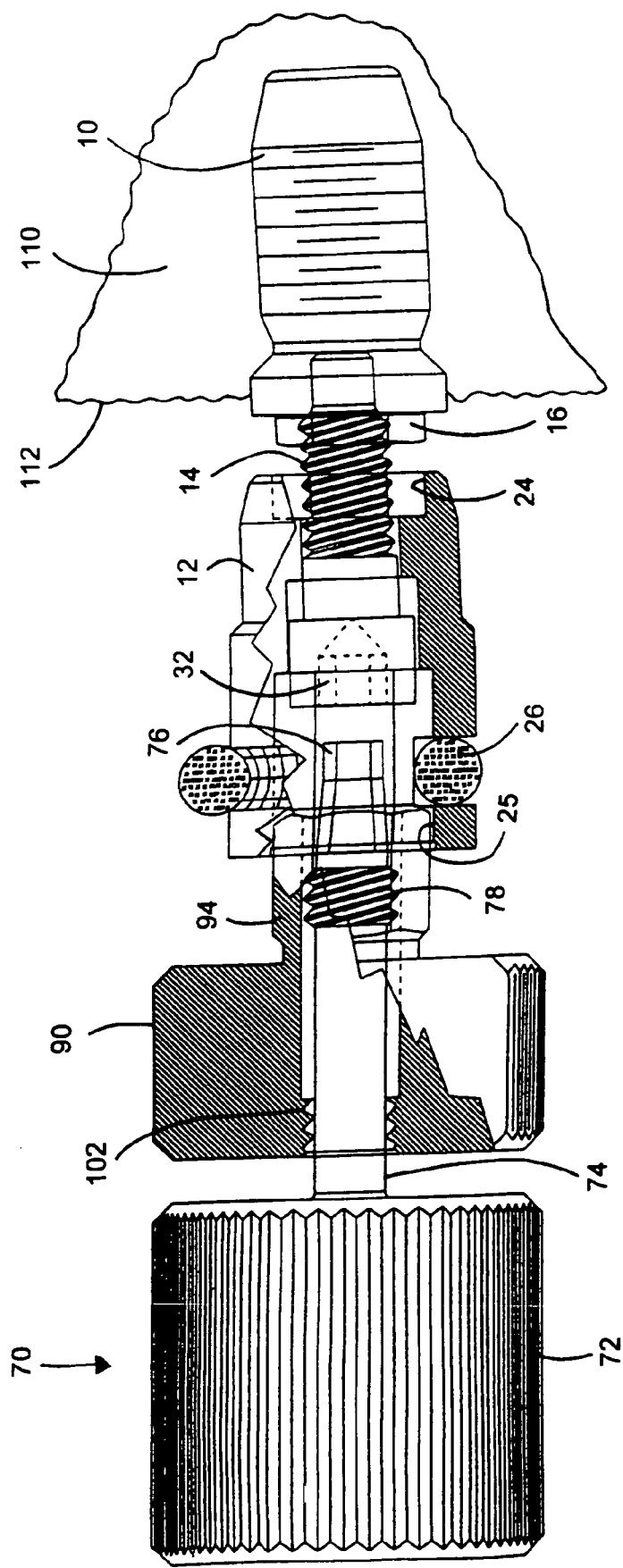
FIG. 7 illustrates the driver of FIG. 4 and the guide of FIGS. 5a-5b releasing the implant screw from the implant.

FIG. 7 illustrates, in an exploded view, the process of the carrier 12 being removed from the implant 10 after the implant 10 is installed into its final position in the bone 110 with the upper flange portion of the implant 10 being near the upper surface 112 of the bone 110. To remove the carrier 12 from the implant 10, the driver 70 with the selected guide 90 is placed above and in axial alignment with the combination of the carrier 12 and the implant 10. The combination of the driver 70 and the guide 90 is then lowered such that the engaging portion 94 of the guide 90 fits within the socket 25 of the carrier 12. Due to the non-rotational engagement of the engaging portion 94 and the socket 24, the guide 90 does not rotate relative to the carrier 12. Although the engaging portion 94 of the guide 90 is partially set out from the socket 25 in the exploded view of FIG. 7, the engaging portion 94 is usually inserted entirely in the socket 25. Consequently, a section of the engaging portion 94 contacts the O-ring 26. Furthermore, the engaging portion 94 may have a circumferential groove into which the O-ring 26 would be positioned (like the groove 131 in FIG. 8*a*).

The clinician then pushes the head 72 of the driver 70 downward such that the fitting 76 on the lower portion of the shank 74 is forced into non-rotational engagement with the driver socket 32 of the implant screw 14. Because of its unique tapered shape, the fitting 76 fits within the driver socket 32 without the need for an excessive amount of force or rotation. With the clinician grasping the head 72 and the flats 98 (FIG. 5*b*) of the guide 90, the clinician then rotates the head 72 while holding the guide 90 non-rotationally. Because the guide 90 is non-rotationally attached to the carrier 12, which is itself non-rotationally attached to the implant 10 through the implant socket 24 and the manipulating fitting 16, any rotation imparted on the head 72 causes only the implant screw 14 to rotate; the implant 10 does not rotate. In other words, the guide 90 holds the assembly of the carrier 12 and the implant 10 steady as the implant screw 14 is removed or installed.

As the implant screw 14 rotates, it is threaded out of the implant 10 such that there is no component holding the carrier 12 onto the implant 10. Additionally, because there is no rotation imparted on the implant 10, its final installation position within the bone 110 remains constant. When the implant screw 14 is fully unthreaded from the implant 10, the driver 70 and the guide 90 are removed from the patient's mouth. Because the carrier 12 is now free of the implant 10, the axial movement of the driver 70 and the guide 90 also removes the carrier 12 because of the tight fit of the engaging portion 94 in the socket 25 due to contact with the O-ring 26. If the O-ring 26 is not designed to provide tight engagement with the engaging portion 94, then the clinician simply releases the carrier 12 from the implant 10 and removes it from the mouth once the implant screw 14 has been threadably removed from the implant 10.

In the event that the clinician finds it difficult to grasp the guide 90 and restrain it from rotational movement, the clinician can utilize another tool, such as a wrench, to grasp the two flats 98 (FIG. 5*b*) such that the clinician's fingers are only needed to manipulate the head 72 of the driver 70. In this situation, one of the clinician's hands is holding the wrench while the other is simply unscrewing the implant screw 14 with the driver 70.

The relationship of the threaded region 102 of the guide 90 and the threaded portion 78 of the driver 70 is shown in FIG. 7. Once the threaded region 102 of the guide 90 is threaded over the threaded portion 78 on the shank 74 of the driver 70, the guide 90 cannot be removed from the driver 70 without rotating the guide 90 relative to the driver 70 while the threaded region 102 is positioned directly adjacent to the threaded portion 78. In essence, the guide 90 is held captive on the driver 70 between the threaded portion 78 and the head 72. In typical operation, as the clinician is utilizing the driver 70 and the guide 90 to remove the implant screw 14 from the implant, the threaded region 102 is axially spaced from the threaded portion 78. Thus, the rotation of the driver 70 relative to the guide 90 in that situation does not cause engagement of the threaded region 102 and the threaded portion 78. The guide 90 is not released from the driver 70 during removal or insertion of the implant screw 14 due to the positioning of the threaded portion 78 and the threaded region 102.

Until now, the discussion has focused on the installation of the implant 10 and removal of the carrier 12 therefrom after installation. The combination of the implant 10 and the carrier 12 can, however, also be used with additional components to take an impression of the patient's mouth during first stage surgery after the implant 10 has been installed into its final position within the jawbone. The components used to perform this function are described with reference to FIGS. 8-11.

In FIG. 8, an impression coping 120 is illustrated. The impression coping 120 includes a body 122 which separates an indexing region 124 from a boss 126 that engages the carrier 12. The indexing region 124 includes a plurality of recesses 127 which are shown best in FIG. 8b. The recesses 127 form in the overlying impression material a unique shape which allows for the proper orientation of the impression coping 120 when it is reinserted into the impression material after the impression is taken. The recesses 127 are circumferentially symmetric about the central axis of the impression coping 120, and each recess 127 is aligned with a corresponding face 128 on the boss 126. The details of this impression coping 120 and its associated bolts are disclosed in U.S. Pat. No. 5,685,715 entitled "Self-Indexing Transfer Impression Coping," which is herein incorporated by reference.

The plurality of faces 128 give the boss 126 a non-round cross-sectional shape. Because the boss 126 is to be inserted into the socket 25 (FIG. 1) of the carrier 12, the boss 126 has the same cross-sectional configuration as the socket 25. Additionally, the boss 126 includes a slit 130 extending therethrough. The slit 130 allows for the expandability of the boss 126 when it is engaged by the bolt described below in FIGS. 9 and 10. To further assist in retention of the coping 120 on the carrier 12, a groove 131 may extend circumferentially around the boss 126 and engage the O-ring 26 within the socket 25 to assist in locking the impression coping 120 on the carrier 12. In any event, the lower end surface of the body 122 is to engage the upper end surface of the carrier 12 adjacent to the opening of the socket 25.

A bore 132 extends through the body 122, the indexing region 124, and the boss 126. The bore 132 includes a threaded portion 134 for threadably engaging a corresponding threaded region of the bolt which mates with the impression coping 120. Within the indexing region 124 is an annular ledge 136 for engaging the head of the bolt. The annular ledge 136 is best seen in FIG. 8b and is manufactured in various sizes depending on the size of the bolt to be used with the coping 120. As described below with reference to FIGS. 9 and 10, the impression coping 120 can be used as both a transfer coping and a pick-up coping.

Figure 9:
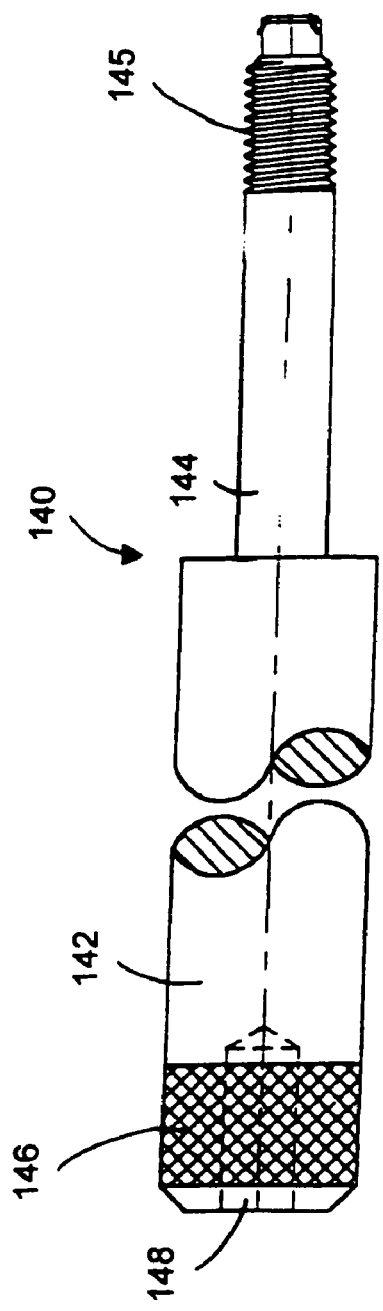
FIG. 9 illustrates a pick-up bolt used with the impression coping of FIG. 8.

In FIG. 9, a pick-up bolt 140 is illustrated. The pick-up bolt 140 includes an elongated head 142 connected to a shaft 144 having at its lower end a threaded region 145. At the upper end of the elongated head 142 is a knurled portion 146, which is a surface the clinician can easily grip. The elongated head 142 also includes an internal fitting 148 to mate with a correspondingly-shaped tool, such as the fitting 76 of the driver 70.

When the pick-up bolt 140 is used with the impression coping 120, the boss 126 of the impression coping 120 is first inserted into the upper end of the carrier 12 at its socket 25. The pick-up bolt 140 is then inserted through the bore 132 of the impression coping 120. The threaded region 145 of the pick-up bolt 140 threadably engages the threaded portion 134 of the bore 132. As the pick-up bolt 140 is threaded into the impression coping 120, the threaded region 145 eventually reaches the threaded portion 134 located within the boss 126. As this occurs, the boss 126 is expanded radially outward such that it is forced into a press-fit, frictional engagement with the socket 25 of the carrier 12. Thus, the impression coping 120 is fixedly mounted on the carrier 12 by the use of this pick-up bolt 140. This allows the clinician to use an open tray method of making an impression whereby, after the impression is taken, the pick-up bolt 140 is removed while the impression material remains at the site. The impression coping 120 is then "picked up" as the impression material is removed.

The carrier 12 is removed from the implant 10 and then reunited with the impression coping 120 within the impression material such that both the impression coping 120 and the carrier 12 are used to create the model used to develop the prosthetic tooth. The carrier 12 is attached to the implant analog that is used to produce the stone model replicating the patient's mouth.

Figure 10:
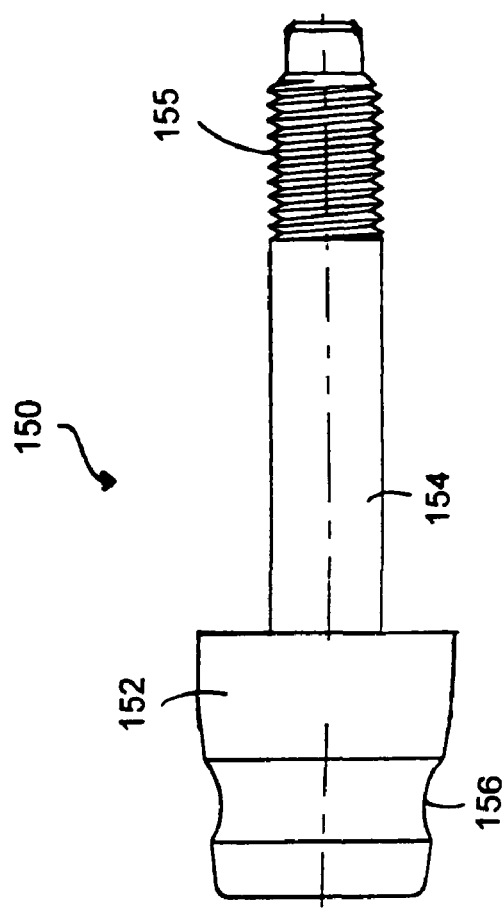
FIG. 10 illustrates a transfer bolt used with the impression coping of FIG. 8.

In FIG. 10, a transfer bolt 150 is illustrated. The transfer bolt 150 includes a short head 152, a shank 154, and a threaded region 155 at the lower end of the shank 154 opposite the head 152. The short head 152 decreases in its diametric dimension from the region near the shank 154 to its outer extremity. The short head 152 may also include a groove 156 extending therearound, allowing for additional retention of the transfer bolt 150 in the impression material. The diametric width of the short head 152 adjacent the shaft 154 is approximately the same as the diametric width of the annular ledge 136 of the impression coping 120. Thus, when the transfer bolt 150 is used to affix the impression coping 120 to the carrier 12, the lower surface of the short head 152 engages the annular ledge 136.

When the transfer bolt 150 is used, the combination of the transfer bolt 150 and the impression coping 120 forms a "transfer-type" impression coping. After the threaded region 155 of the transfer bolt 150 is threadably engaged with the threaded portion 134 of the internal bore 132 of the impression coping 120, an impression is taken using a closed tray method. When the impression material is removed from the patient's mouth, the impression coping 120 and the transfer bolt 150 both remain on the carrier 12. The clinician then removes the transfer bolt 150 by rotating the head 152 such that the threaded region 155 is threadably released from the threaded portion 134 of the impression coping 120. Once the transfer bolt 150 is removed from the patient's mouth, the impression coping 120 can be removed. The clinician then releases the carrier 12 from the implant 10, as described previously, and reunites the impression coping 120 on the carrier 12 by the use of the transfer bolt 150. The combination of the transfer bolt 150, the impression coping 120, and the carrier 12 is then attached to an implant analog in the laboratory. The impression material is then reinserted over the transfer bolt 150, the impression coping 120, and the carrier 12 such that a stone model can be built which replicates the prevailing conditions in the patient's mouth.

It should be noted that the transfer bolt 150 can be screwed onto and removed from the impression coping by use of a tool which has a tapering socket that replicates the tapering of the short head 152. Such a tool may also include a retention O-ring which engages the groove 156, thereby locking the tool onto the transfer bolt 150. Thus, the clinician can easily attach and remove the transfer bolt 150 from the impression coping 120. A corresponding taper could be used on the pick-up bolt 140 at its upper end so that the same tool could be used with both the pick-up bolt 140 and the transfer bolt 150.

As can be seen, the impression coping 120 is a very versatile component in that it can be used as both a transfer-type coping and a pick-up-type impression coping, depending on the bolt used. Additionally, because the recesses 127 of impression coping 120 are aligned with faces 128, the recesses 127 are also aligned with the manipulating fitting 16 of the implant 10 (FIG. 1). This is due to the fact that the socket 25 of the carrier 12 has its surfaces aligned with the implant socket surfaces 24. Because each recess 127 is aligned with a corresponding face 128 and the socket 25 is aligned with the manipulating fitting 16, the combination of the impression coping 120 and the carrier 12 can easily be correctly oriented in the impression material when the carrier 12 and impression coping 120 are mounted on the implant analog. Actually, after the carrier 12 and the impression coping 120 are attached, three of the possible six orientations on the implant analog will yield the correct orientation due to the symmetry.

Figures 11A, 11B:
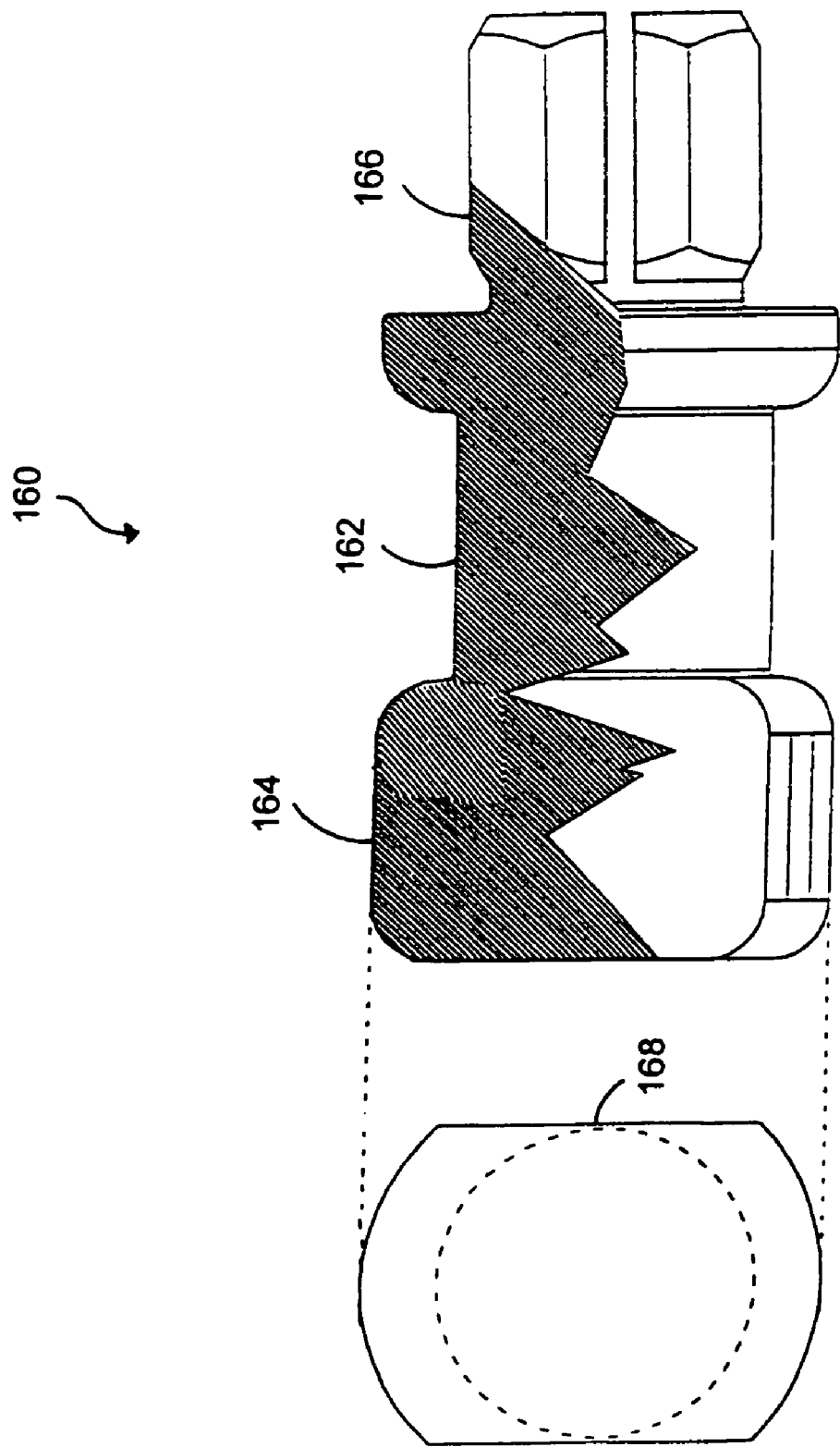
FIGS. 11a-11b illustrate an alternative pick-up impression coping that can be used with the carrier of the present invention.

In FIGS. 11a and 11b, an alternative pick-up coping 160 is illustrated. The pick-up coping 160 includes a body 162 which separates a head portion 164 from an expandable boss 166. The head portion 164 includes a pair of flats 168 allowing for the indexing of the pick-up coping 160 within the impression material. As with the previously described impression coping 120, the boss 166 expands outward when the pick-up bolt 140 in FIG. 9 is threaded therein. Thus, although not illustrated, the pick-up coping includes an internally threaded bore whose threads extend into the region of the boss 166. The pick-up coping 160 can utilize the same impression techniques as those described with reference to FIG. 9. Although the expandable boss 166 does not show a circumferential groove as did the impression coping 120, the expandable boss 166 in the pick-up coping 160 may include a similar groove to assist in locking the expandable boss 166 within the socket 25 of the carrier 12 through engagement with the O-ring 26.

As has been previously stated, once the implant 10 has been installed into its final position within the living jawbone, there are two methods which can be employed by the clinician utilizing the components described in FIGS. 1-11. First, the clinician can simply remove the carrier 12 from the implant 10. Alternatively, the clinician can attach the impression coping 120 to the carrier 12 and take an impression of the areas around the impression coping 120 and the carrier 12 immediately above the implant 10. If the latter option is employed by the clinician, the clinician then removes the impression coping 120 and the carrier 12 and reunites these two components before reinserting them back into the impression material.

Regardless of the method chosen by the clinician, the result is an implant 10 fully inserted into the jawbone with the overlying gingiva having therethrough an aperture that exposes the manipulating fitting 16 of the implant 10. To complete the first stage surgery, the clinician installs onto the implant 10 a commonly known healing cap which covers the threaded bore 18 (FIG. 1). The overlying gingiva is then sutured to allow for its healing, as well as the osseointegration of the implant 10.

During typical stage two surgery, the gingiva overlying the implant 10 is reopened so as to expose the healing cap positioned on the implant 10. The healing cap is then removed and a gingival healing abutment is attached to the implant 10. This allows for the healing of the gingiva tissue around the healing abutment directly above the implant 10 to a shape that is preferably similar to the profile from which the natural tooth emerged from the gingiva.

If an impression was taken during first stage surgery, the clinician will have had time to develop a prosthetic tooth. Instead of utilizing a healing abutment, the clinician can install the prosthetic tooth directly on the implant. Usually, this prosthetic tooth is a temporary one and another impression may be taken to develop an accurate final dentition.

But, in some situations where the final position of the overlying gingiva can be predicted, the artificial tooth that is replicated from the model produced in first stage surgery can be so accurate that a permanent dentition can be developed and installed onto the implant 10 at second stage surgery. In this situation, the patient enters the clinician's office only twice; the first time for installing the implant, the second time for installing the permanent dentition.

FIGS. 12a-12d illustrate an alternative embodiment of an implant delivery system 180. The implant delivery system 180 includes a dental implant 182, a carrier 184, and a screw 186. As in previous embodiments, the implant 182 includes an external hexagonal fitting 188 at its upper end.

The carrier 184 includes a through bore 190 that has a polygonal socket 192 at its upper end. The polygonal socket 192 has an interrupted surface due to an internal thread 194 that also resides at the upper end of the through bore 190. Because the through bore 190 has the polygonal socket 192 in the location of the internal thread 194, the internal thread 194 has a depth that varies depending on whether it is measured on a flat of the polygonal socket 192 or in a corner of the polygonal socket 192. As shown in FIG. 12, the internal thread 194 is single lead thread, making multiple terms within the through bore 190. A multi-lead thread could be used, however, in place of the single lead internal thread 194.

The carrier 184 has an external surface that includes an upper circumferential groove 200 and a lower circumferential groove 202. The upper circumferential groove 200 is located at 3 mm from the lowermost end of the carrier 184 and serves as a visualization marker for the clinician so that the clinician knows the depth of insertion of the implant 182. The lower circumferential groove 202 is also a visualization marker for the clinician in that it allows the clinician to know the location of the implant cover screw relative to the implant since the distance between the lower circumferential groove 202 and the lower surface of the carrier 184 is chosen to be the same as the height of the implant cover screw (for example, 1 mm). Additionally, the external surface includes a plurality of radial grooves 206 that are aligned with the internal flats of the polygonal socket 192. Because each of the flats of the polygonal socket 192 are aligned with a flat of the hexagonal socket (FIG. 12d) that mates with the hexagonal boss 188 of the implant 182, each of the radial grooves 206 is also aligned with one of the flats of the hexagonal boss 188 of the implant 182. Accordingly, as the clinician installs the implant 182 with a tool that exerts torque on the carrier 184, he or she can visualize the location of each of the flats of the underlying hexagonal boss 188 due to the radial grooves 206. The radial grooves 206 can be replaced by simple markings, such as the markings 39 of FIG. 2B.

Figure 12B:
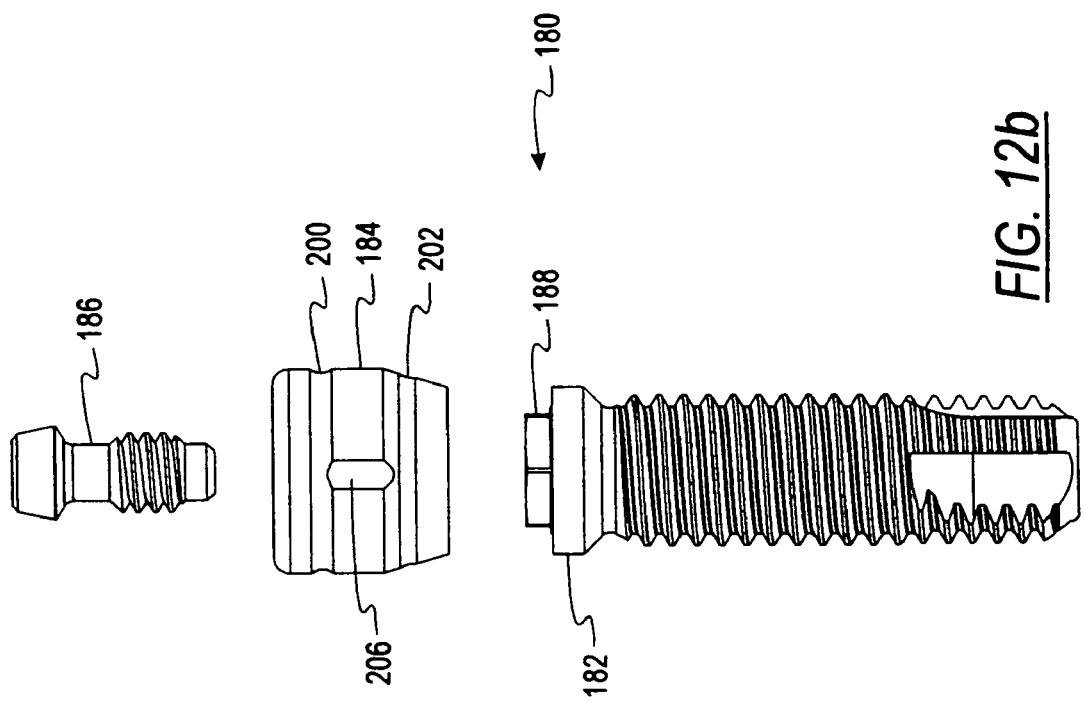
FIGS. 12a-12d illustrate another embodiment of the implant delivery system in which the carrier includes internal threads for receiving secondary components.
Figure 12A:
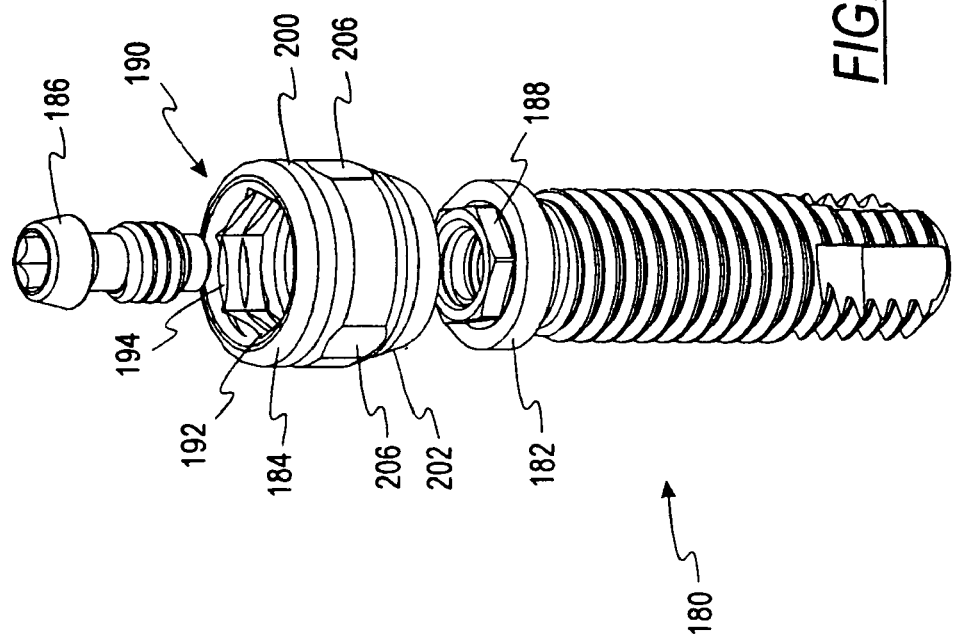
Figure 12C:
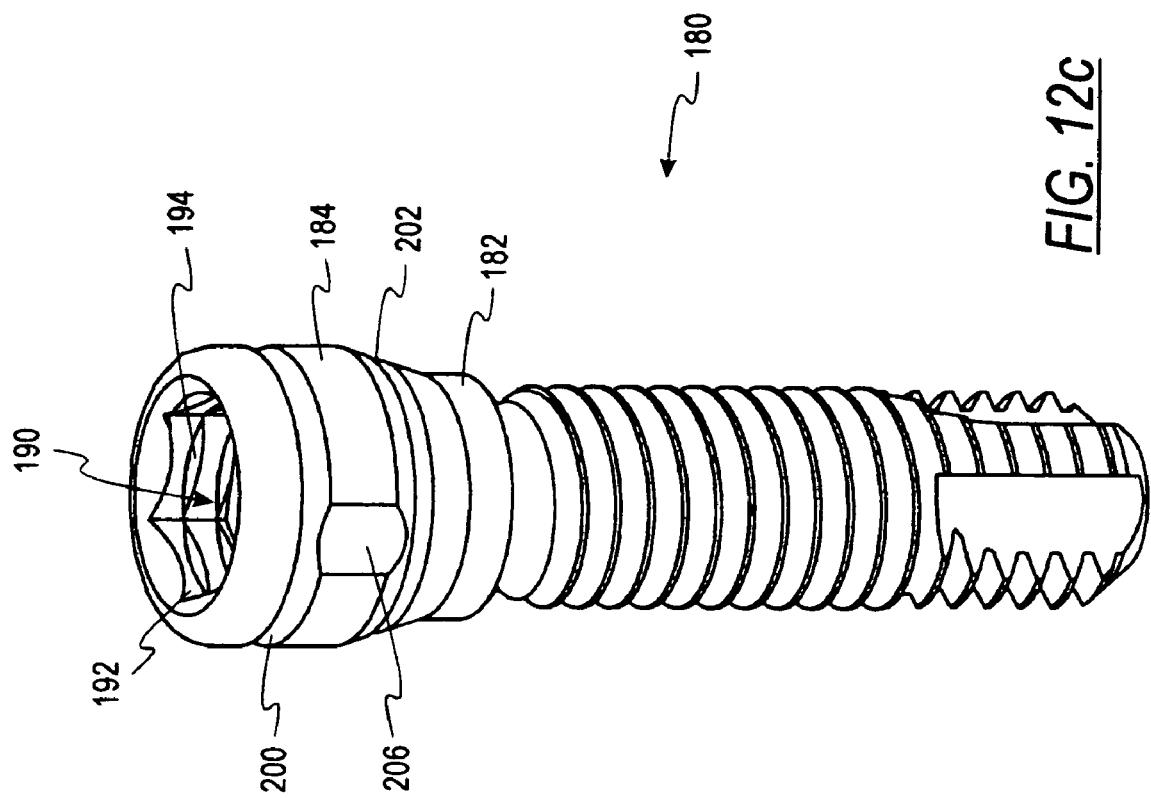
Figure 12D:
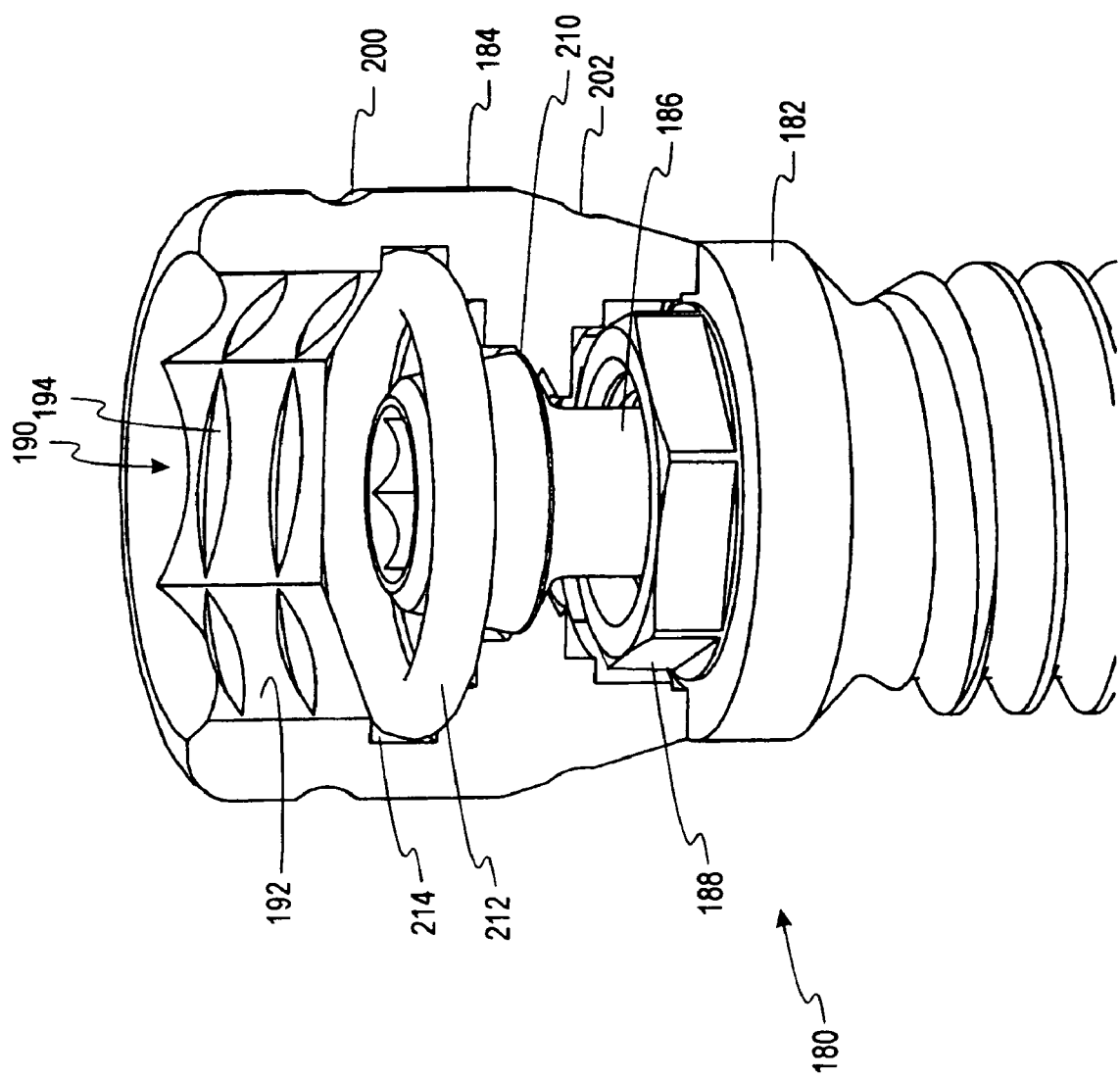

Referring specifically to FIG. 12d, the carrier 184 includes an internal shoulder 210 against which the head of the screw 186 is positioned when the carrier 184 is attached to the dental implant 182. An O-ring 212 resides within a groove 214 on the interior wall of the carrier 184 below the polygonal socket 192. The O-ring 212 serves as a retention mechanism that allows a tool to remain coupled to the combination of the carrier 184 and a dental implant 182 during the installation process. Therefore, the clinician inserts such a tool into the carrier 184 and moves the combination of the carrier 184 and the dental implant 182 to any location without having to touch the implant 182, which is typically sterile. The O-ring 212 can also be replaced with a C-ring having resilient properties.

FIGS. 13a-13b illustrate a tool 220 having a driver attachment end 222, a shank 224, and a carrier attachment end 226. The driver attachment end 222 can be one of many types of structures that is useful for engaging dental drivers, and is shown as a standard ISO-latch system commonly used in dentistry. The carrier attachment end 226 includes an external polygonal fitting that is divided into a tapering section 228 and a non-tapering flat section 230. The tapering section 228 is wider at the end adjacent to the shank 224 and allows the tool to tightly engage the top edge of the polygonal socket 192 of the carrier 184, as will be discussed in more detail in FIG. 14. The carrier attachment end 226 also includes a circumferential groove 232 that engages the O-ring 212 within the carrier 184. The lowermost end of the carrier attachment end 226 has an opening 234 into which the head of the screw 186 is positioned during installation.

Figure 14:
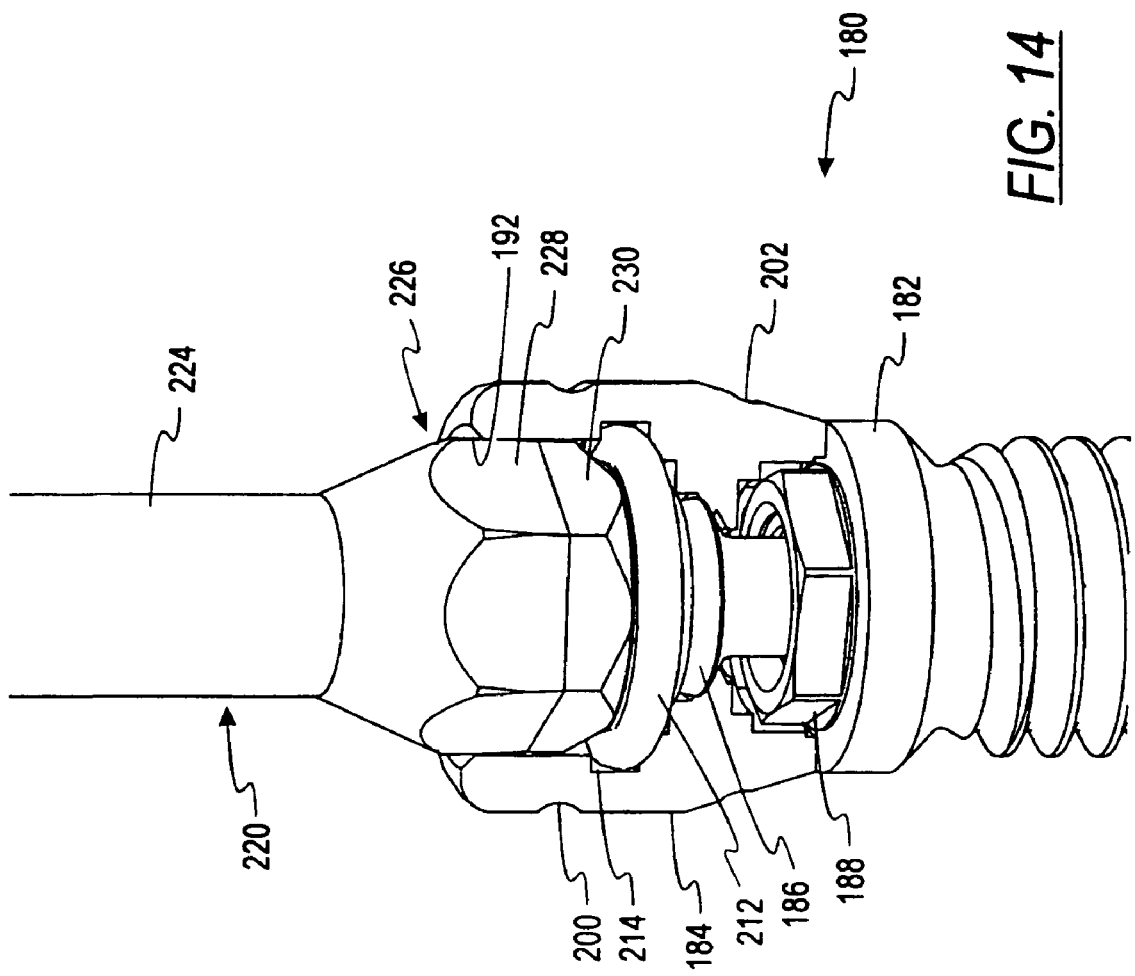
FIG. 14 illustrates the tool of FIG. 13 in use with the implant delivery system of FIG. 12.

FIG. 14 illustrates the implant delivery system 180 being engaged by the tool 220. The carrier 184 is mechanically coupled to the implant 182 via the screw 186. The opening 234 at the lowermost end of the carrier attachment end 226 is positioned within the polygonal socket 192 of the carrier 184 and fits over the head of the screw 186 without engaging it. The non-tapering flat section 230 is dimensioned to fit within the polygonal socket 192. The tapering section 228 tapers outward such that, on one point on its surface, an interference fit is established with the top edge of the polygonal socket 192. The O-ring 212 fits within the circumferential groove 232 below the non-tapering flat section 230. Due to the interference fit of the tapering section 228 and the engagement of the O-ring 212 to the groove 232, the tool 220 can be used to move the entire implant delivery system 180 without the clinician having to touch any part of the sterile implant 182.

Once the clinician delivers the implant 182 to the appropriate site within the patient's mouth, the tool 220 is used to provide torque to the implant 182 via the carrier 184 to install the implant 182 into the bone of the patient. As the clinician is installing the implant 182, he or she observes the locations of the upper circumferential groove 200 and the lower circumferential groove 202 on the carrier 184 to ensure that the implant 182 is being installed to the proper depth. Once the implant 182 has been installed to the proper depth, the tool 220 is removed from the carrier 184. Due to tight engagement between the implant 182 and the bone, the force required to remove the tool 220 from the carrier 184 does not disturb the position of the implant 182 within the bone. At this point, the carrier 184 is extending through the gingival tissue above the bone.

When the tool 220 is used to install the implant 182 into bone, the torque must be applied across a reasonable amount of area. Accordingly, it is preferred that as much area of the polygonal fitting 192 as possible receives torque when installing the implant into bone. The implant delivery system 180 accomplishes this by providing a tapered region to the head of the screw 186. Because the opening 234 in the carrier-engaging section 226 fits over the tapered head of the screw 186, the tool 220 can be inserted further into the carrier 184 to maximize the amount of contact area on the polygonal fitting 192 that is to receive the torque. Hence, the carrier 184 can be made much shorter than prior art carriers so that it serves the purpose of a healing abutment as is described below. For example, the carrier 184 can have a height that is 4 mm or less.

Figure 15A:
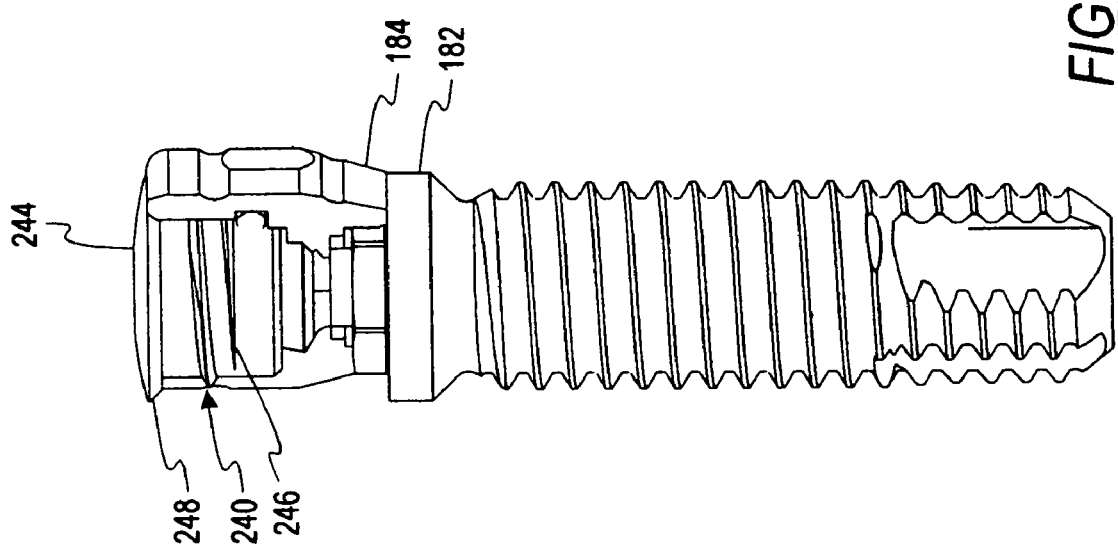
FIGS. 15a and 15b illustrate the carrier being used as part of a healing abutment.
Figure 15B:
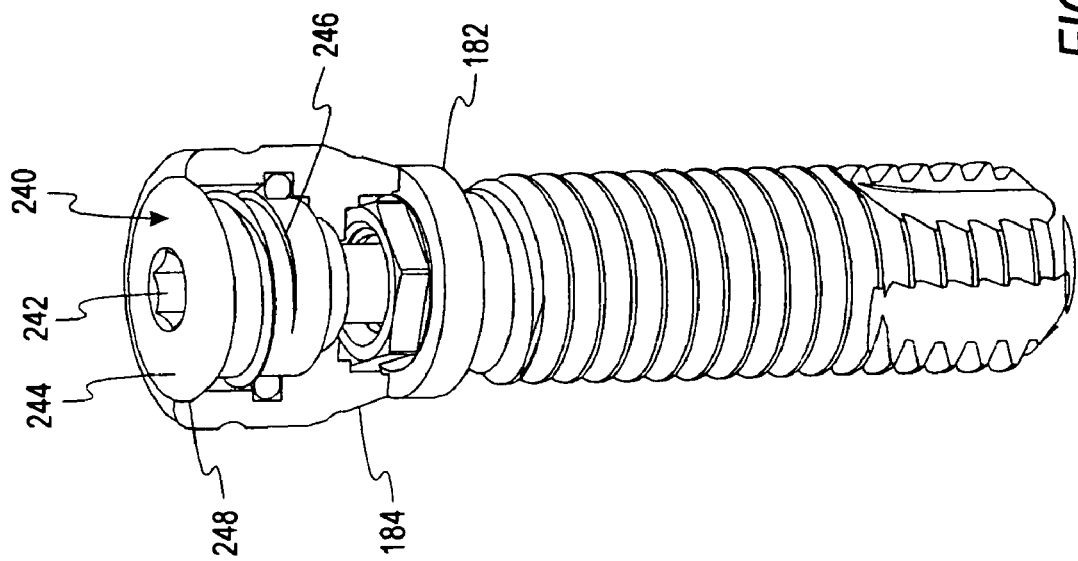

Because the carrier 184 has the general shape of a typical healing abutment, the carrier 184 is also used with a healing plug 240 of FIGS. 15a-15b. The combination of the carrier 184 and the healing plug 240 is a gingival healing abutment around which the gingiva heals to create an aperture through which the final prosthesis will emerge. The healing plug 240 includes a socket 242 in its upper surface 244 and threads 246 of its exterior side. The threads 246 engage the internal threads 194 of the carrier 184 as the clinician rotates the healing plug 240 into the carrier 184. The healing plug 240 includes an undercut 248 that mates with an external bevel on the carrier 184 to provide a seal at this interface. The plug 240 is substantially flush with an upper surface of the carrier 184. When the carrier 184 serves as a part of the healing abutment, it is desirable to have it be of a color that is aesthetically pleasing. Thus, the carrier 184 can have a titanium nitride coating or can be anodized to a gold hue.

Figure 16A:
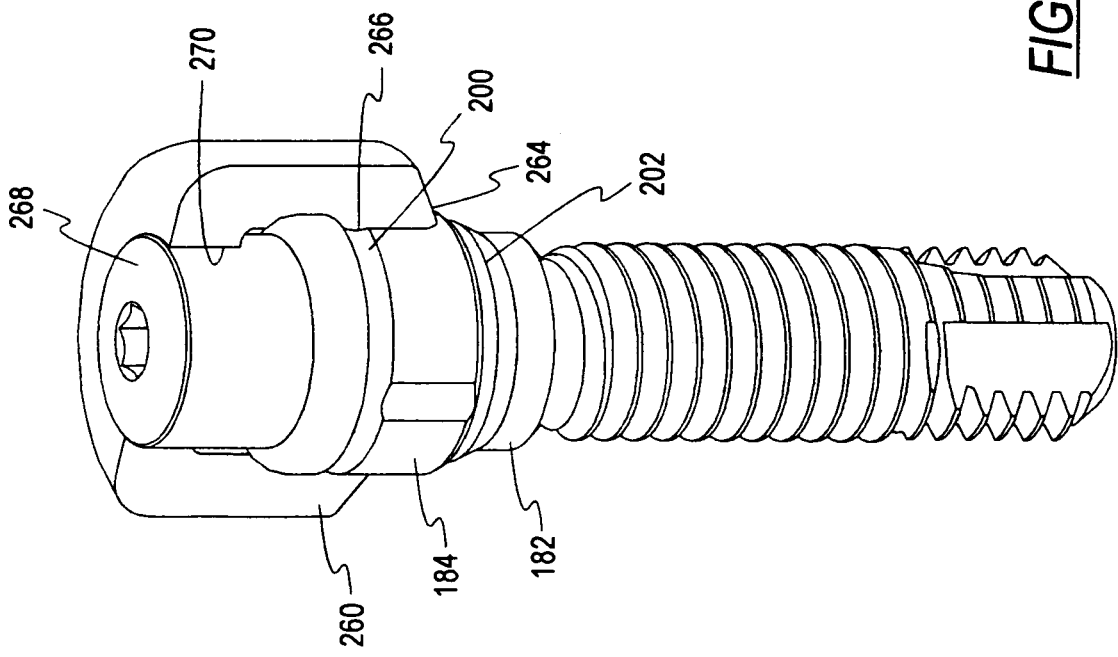
FIGS. 16a and 16b illustrate the carrier being used as part of an alternative healing abutment having a wider diameter.
Figure 16B:
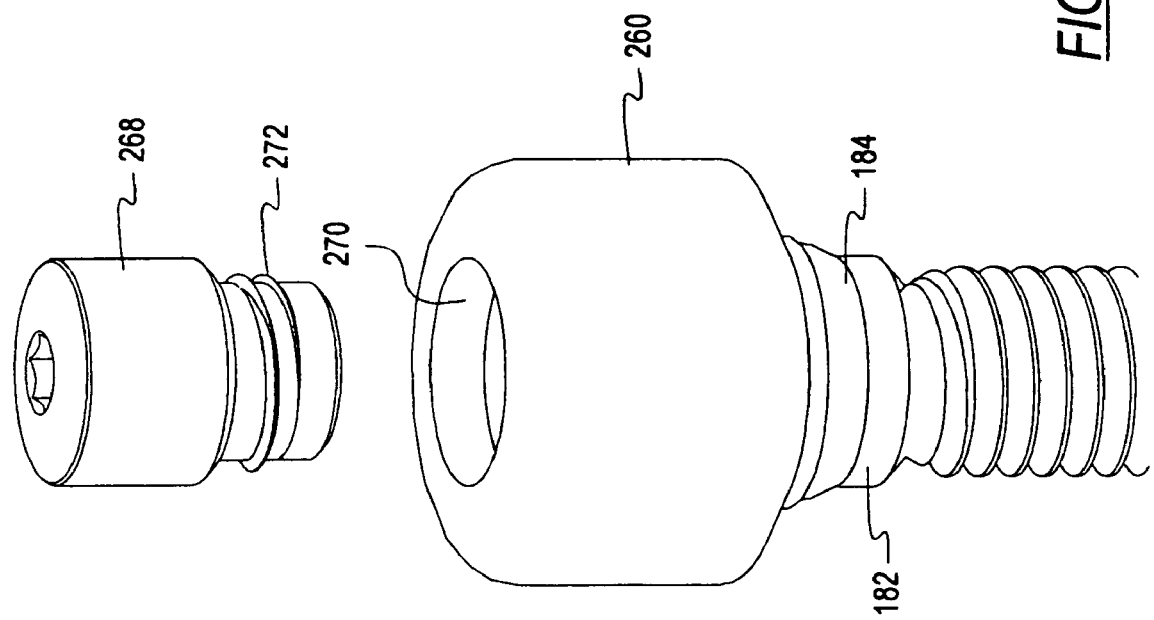
Figure 17A:
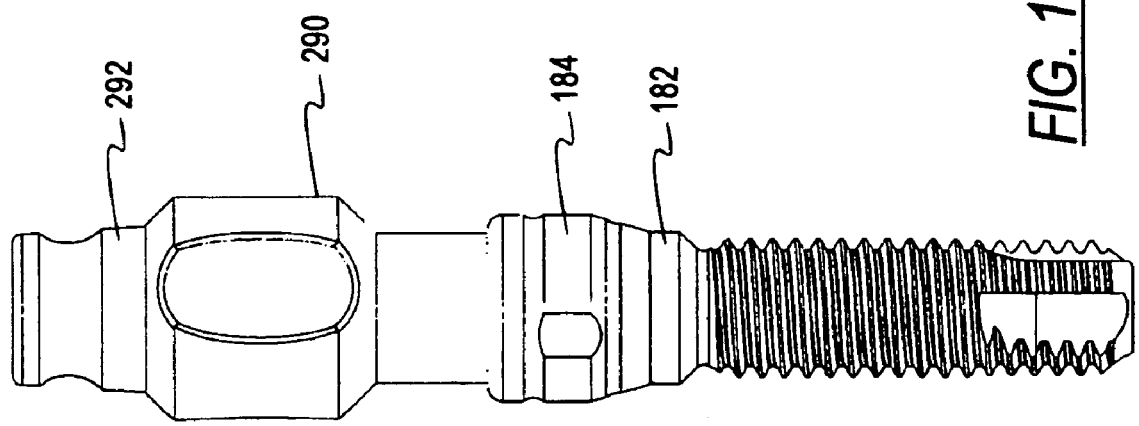
FIGS. 17a-17d illustrate the carrier of FIG. 12 being used as part of an impression component.
Figure 17B:
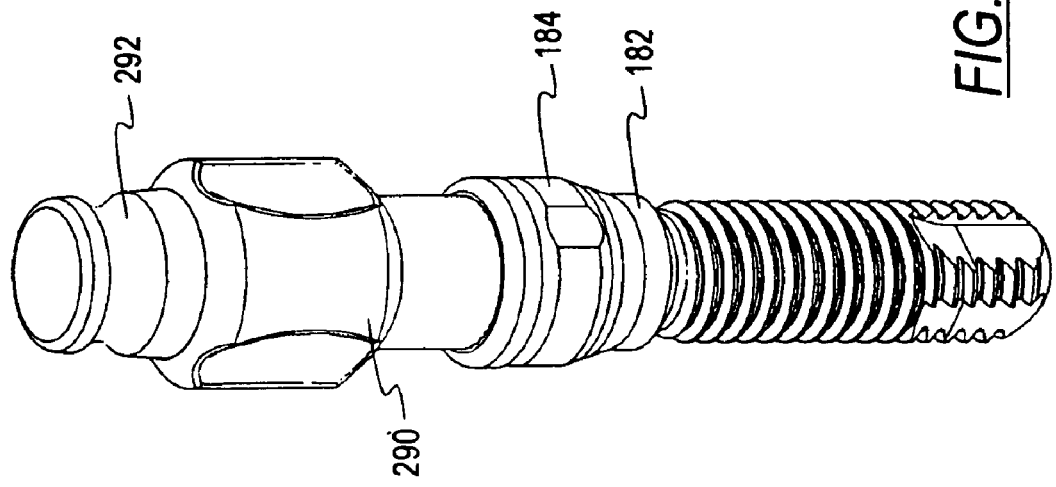
Figure 17C:
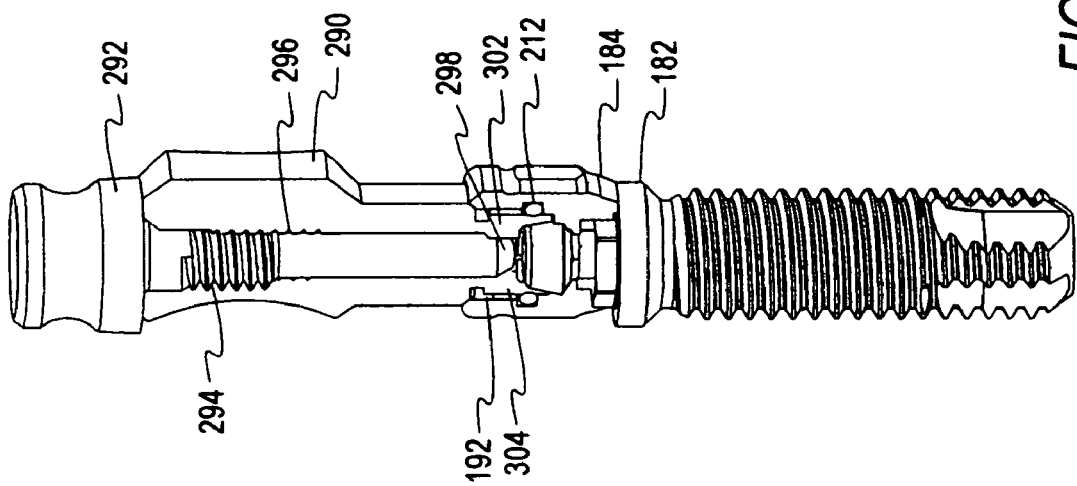
Figure 17D:
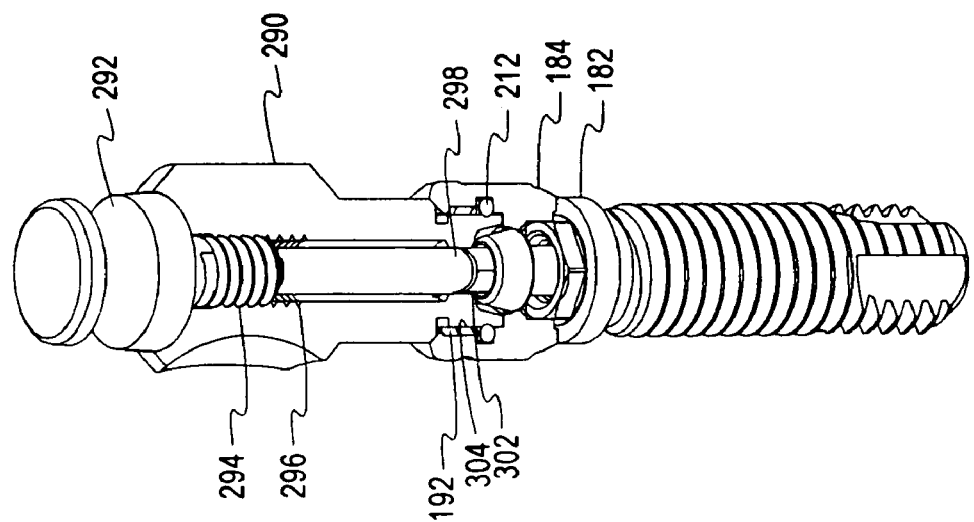

FIGS. 16a-16b illustrate an alternative embodiment where the carrier 184 is used as part of the gingival healing abutment. Here, a body 260 slides over the carrier 184 and includes a first protrusion 264 and a second protrusion 266 that mate with the lower circumferential groove 202 and the upper circumferential groove 200, respectively. An elongated healing plug 268 fits through the opening 270 of the body 260 and includes the threads 272 at its lower end that mate with the internal threads 194 of the carrier 184. Thus, if the clinician encounters a situation where a larger aperture is needed through the gingiva, the body 260 is placed over the carrier 184 and the plug 268 is inserted for the opening 270 in any body 260. The body 260 is preferably made of a resilient polymeric material.

FIGS. 17a-17d illustrate the carrier 184 being used as part of an impression coping system. The system shown in FIGS. 17a-17d is similar to the impression systems previously discussed. An impression component 290 fits into the polygonal socket 192 of the carrier 184 and an impression screw 292 is then inserted into the impression component 290. The impression screw 292 includes the external threads 294 below its head that mate with the internal threads 296 in the impression component 290. As the threads 294, 296 engage, the lowermost end 298 of the impression screw 292 contacts a shoulder 302 within the impression component 290. The force exerted by the lowermost end 298 on the shoulder 302 causes the lower end of the impression component 290 to expand outward. Because the lower end of the impression component 290 has a polygonal surface 304 that mates with the polygonal socket 192, the impression component 290 is tightly engaged with the carrier 184. Additionally, it should be noted that the impression component 290 is held within the carrier 184 by the O-ring 212 prior to introducing the impression screw 292 into the impression component 290. Thus, the O-ring 212 temporarily supports the impression component 290 on the carrier 184. Further, because of the tapered head of the screw 186, the impression component 290 fits further down into the polygonal fitting 192 of the carrier 184, as can be seen best in FIGS. 17c-17d.

The clinician may elect to take an impression immediately after installing the implant 182 into the bone. In this situation, the clinician employs the impression component 290 and impression screw 292 after the tool 220 has been removed from the carrier 184. After the impression is made and the impression component 290 and the impression screw 292 are removed, the clinician may attach a supplemental carrier to the impression component 290 and the impression screw 292 that will be used by the laboratory with the impression to make the prosthesis. The clinician can then attach the healing plug 240 of FIGS. 15a-15b to the carrier 184. If the clinician chooses to have a larger gingival aperture and employs the combination of the body 260 and the healing plug 268 of FIGS. 16a-16b, then the clinician should preferably take the impression while the body 260 and the plug 268 are on the carrier 284.

The clinician may also follow a more typical impression procedure and take the impression after the gingiva has healed. In this situation, the carrier 184 first serves as part of the healing abutment (i.e., as shown in FIGS. 15-16) and then serves as part of an impression component. After the impression is taken, the clinician uses a supplemental carrier to attach to the impression components that will be sent to the laboratory with the impression. It is the orientation of the supplemental carrier on the impression component that establishes the relative position of the hexagonal boss 188 of the implant 182 within the impression.

While the internal threads 194 of the exterior 184 have been described as being useful with healing components (FIGS. 15-16) to make a healing abutment, the internal threads 194 can also be useful for taking an impression with an impression component when multiple units are being restored. When multiple units are being restored and one impression is taken of all units, the orientation of the hexagonal boss 188 on the implant 182 becomes irrelevant. In that situation, an impression component can simply be screwed into the internal threads 194 of the carrier 184. Consequently, the internal threads 194 would mate with the external threads of an impression component and an impression would be taken of that impression component and the carrier 184.

The implant delivery system 180 has been described thus far in situations where the implant 182 has an external hexagonal boss 188 and the carrier 184 has a corresponding hexagonal socket. The implant delivery system 180 can, however, be modified so that it can be used on implants having an internal hexagonal socket, not the external hexagonal boss 188. To do so, the carrier 184 includes an elongated hexagonal boss that fits into the internal socket of the implant. Once this modification has been made, the modified carrier can be used as part of a gingival healing component or an impression component.

Figure 18B:
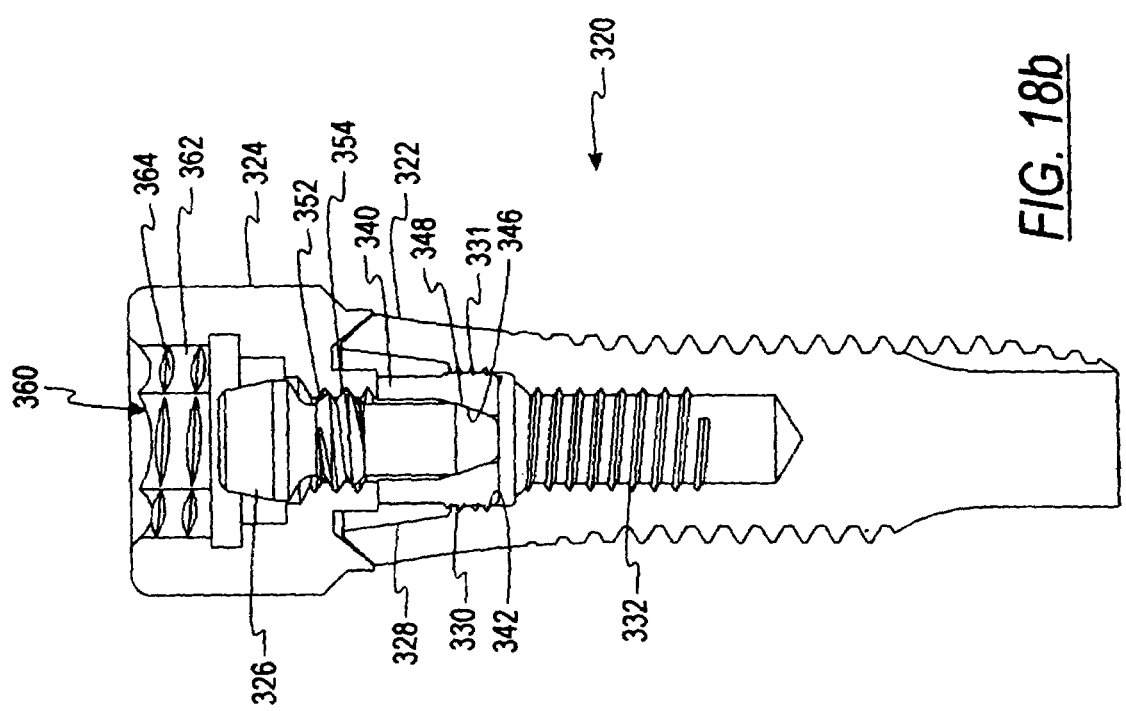
FIGS. 18a-18b illustrate an implant delivery system for use on an implant having neither an internal nor an external polygonal fitting.
Figure 18A:
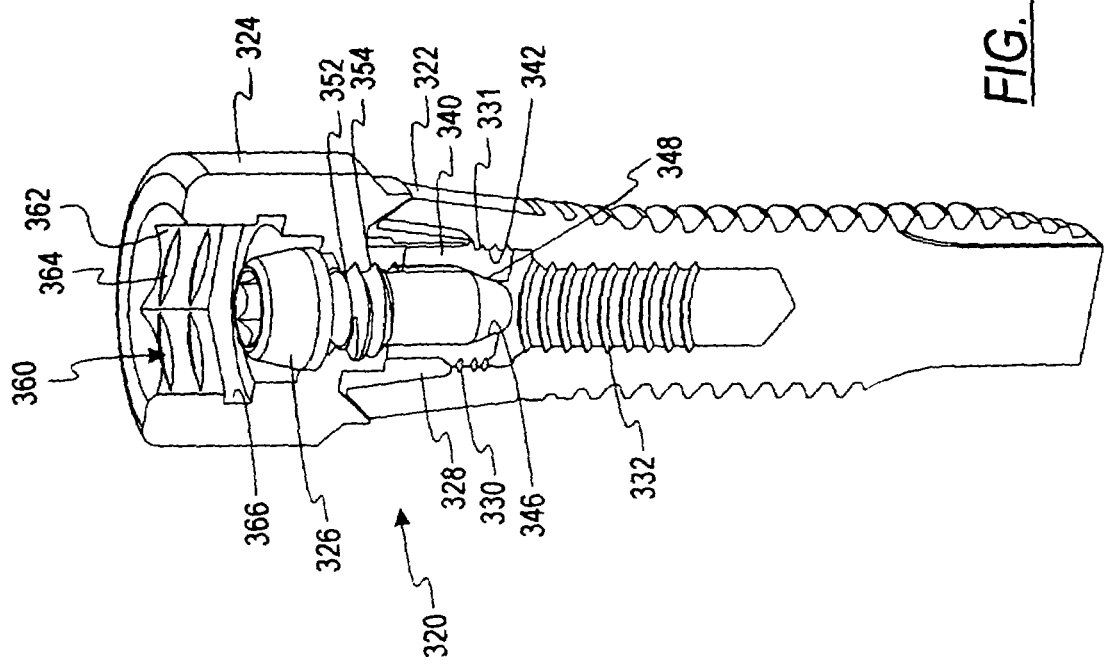

FIGS. 18a-18b illustrate an alternative implant delivery system 320 having an implant 322 that lacks an external hexagonal boss. The implant delivery system 320 includes the implant 322, a carrier 324, and a screw 326. The implant 322 is described in more detail in commonly owned U.S. patent application Ser. No. 09/164,934, which has been allowed and is incorporated herein by reference in its entirety.

The implant 322 includes an internal bore having three distinct internal sections. A tapered entry section 328 is followed by a generally cylindrical section 330 having internal threads 331 which, in turn, is followed by a lower threaded section 332. The carrier 324 includes a lower region 340 having a plurality of resilient fingers that have external threads 342 present thereon. The external threads 342 mate with the internal threads 331 in the generally cylindrical section 330 of the bore of the implant 322.

The end of the screw 326 has a tapered region 346 that engages a complementary shoulder 348 on the lower region 340 of the carrier 324. As the threads 352 of the screw 326 engage an internal threaded surface 354 on the carrier 324, the tapered region 346 of the screw 326 forces the plurality of fingers at the lower region 340 of the carrier 324 to expand outward into tight engagement with the generally cylindrical section 330 of the bore of the implant 322.

The top of the carrier 324 includes a through bore 360 into which the screw 326 is inserted. The through bore 360 includes a polygonal fitting 362 having threads 364 therein, as shown in the previous embodiments of FIGS. 12-17. The through bore 360 also includes a groove 366 into which a resilient structure can be placed, such as an O-ring or a C-ring.

As in the previously discussed, the polygonal fitting 362 receives a tool that exerts torque that is used to install the implant 322 into bone. After the clinician has installed the implant 322 to its appropriate location within the bone, the clinician can simply screw a healing plug into the threads 364 of the through bore 360 so that the carrier 324 serves as a gingival healing component. It should be noted, however, that the implant 322 shown in FIGS. 18a-18b is a transgingival type of implant 322 in which the upper portion of the implant 322 protrudes through at least a portion of the gingival tissue. Thus, the carrier 324 may be useful in situations where the gingival tissue is especially thick or in situations where the clinician prefers a healing component that extends a few millimeters above the gingiva. As in the previous embodiments, the carrier 324 is also useful for taking impressions by combining it with an impression component that is coupled to the carrier through the internal polygonal fitting 362.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A combination of a plurality of carriers and at least one screw for installing an implant at a site in living bone, said implant having an implant anti-rotational feature and external threads for being screwed into said living bone, said combination comprising;

a first carrier that includes a first through-bore and a first anti-rotational fitting for mating with said implant anti-rotational feature of said implant, said first carrier receiving torque to rotate a combination of said implant and said first carrier during installation, said first carrier being of a first length and including a first alignment feature that is aligned with a face of said first anti-rotational fitting for visualizing an angular orientation of said implant anti-rotational feature during installation, said first alignment feature being located on a portion of the first carrier that has the greatest diameter;

a second carrier that includes a second through-bore and a second anti-rotational fitting for mating with said implant anti-rotational feature of said implant, said second carrier receiving torque to rotate a combination of said implant and said second carrier during installation, said second carrier being of a second length and including a second alignment feature that is aligned with a face of said second anti-rotational fitting for visualizing an angular orientation of said implant anti-rotational feature during installation, said second alignment feature being located on a portion of the second carrier that has the greatest diameter;

a third carrier that includes a third through-bore and a third anti-rotational fitting for mating with said implant anti-rotational feature of said implant, said third carrier receiving torque to rotate a combination of said implant and said third carrier during installation, said third carrier being of a third length and including a third alignment feature that is aligned with a face of said third anti-rotational fitting for visualizing an angular orientation of said implant anti-rotational feature during installation, said third alignment feature being located on a portion of the third carrier that has the greatest diameter; and wherein the at least one screw for use in attaching one of said first carrier, said second carrier, and said third carrier to said dental implant;

wherein said first length, said second length, and said third length are different so as to allow a selection of a carrier that is best suited for the patient's conditions.

2. The combination of claim 1, further including at least two implant-insertion tools for imparting rotational movement to said selected carrier and said implant, said implant-insertion tool engaging said carrier device, and wherein one of said implant-insertion tools has a length that is different from the length of the other one of tools.

3. The combination of claim 2, wherein said implant-insertion tool has an end to be engaged by a clinician for manually inserting said implant into said bone.

4. The combination of claim 1, wherein each of said first, second, and third carriers includes a resilient structure within said respective first, second, and third through-bores.

5. The combination of claim 1, wherein said first, second, and third alignment features are located on an expanded top portion of said respective first, second, and third carriers.

6. The combination of claim 5, wherein said first, second, and third alignment features are markings on said expanded top portions.

7. The combination of claim 1, wherein said first, second, and third alignment features are markings.

8. The combination of claim 1, wherein said first anti-rotational fitting, said second anti-rotational fitting, and said third anti-rotational fitting are adapted to mate with a polygonal boss at a top of said implant, said polygonal boss being said implant anti-rotational feature.

9. The combination of claim 1, wherein said first carrier, said second carrier, and said third carrier are adapted to receive said torque from an implant-insertion tool.

10. The combination of claim 9, wherein said implant-insertion tool is coupled to a driver.

11. A method of installing a dental implant at a site in living bone, said implant having an implant anti-rotational feature, said method comprising:
selecting one carrier from a plurality of carriers to be mated with said dental implant, each of said carriers including a through-bore and an anti-rotational fitting for mating with said implant anti-rotational feature of said implant, each of said carriers including an alignment feature that is aligned with a face of said anti-rotational fitting for visualizing an angular orientation of said implant anti-rotational feature during installation, said alignment feature being located on a portion of each of the plurality of carriers that has the greatest diameter, said plurality of carriers being of different lengths;
attaching said selected one of said carriers to said implant by use of a screw extending through said through bore of said selected one of said carriers; and
after said attaching, installing said implant in said living bone by providing torque to said selected one of said carriers.

12. The method of claim 11, further including selecting one of at least two implant-insertion tools for imparting rotational movement to said selected one of said carriers and said implant, said implant-insertion tools having different lengths, said installing includes engaging said selected implant-insertion tool to said carrier device.

13. The method of claim 12, wherein said installing further includes engaging said implant-insertion tool with a power driver.

14. The method of claim 11, wherein said alignment features of said plurality of carriers are located on expanded top portions of said carriers.

15. The method of claim 14, wherein said alignment features are markings on said expanded top portions.

16. The method of claim 11, wherein said implant anti-rotational feature is a polygonal boss at a top of said implant.

17. The method of claim 11, further including, during said installing, visualizing the orientation of said implant anti-rotational feature by use of said alignment feature on said selected carrier.

18. The method of claim 11, wherein said installing includes engaging, with a drive tool, a non-circular socket within said selected carrier.

19. The method of claim 11, wherein each of said carriers includes a resilient structure within said respective through-bores.

20. The method of claim 11, wherein each of said carriers includes an internal torque-recess section in said through-bore for engaging an implant-insertion tool.

21. The method of claim 11, wherein said alignment features are markings.

* * * * *